(12) United States Patent
Horst et al.

(10) Patent No.: US 11,918,765 B2
(45) Date of Patent: Mar. 5, 2024

(54) STYLET WITH IMPROVED THREADABILITY

(71) Applicant: TELEFLEX MEDICAL INCORPORATED, Morrisville, NC (US)

(72) Inventors: Benjamin Horst, Lititz, PA (US); Michael Aman, Sinking Spring, PA (US); Mark Spinka, Jenkintown, PA (US)

(73) Assignee: TELEFLEX MEDICAL INCORPORATED, Morrisville, NC (US)

(*) Notice: Subject to any disclaimer, the term of this patent is extended or adjusted under 35 U.S.C. 154(b) by 0 days.

(21) Appl. No.: 18/116,757

(22) Filed: Mar. 2, 2023

(65) Prior Publication Data

US 2023/0201534 A1    Jun. 29, 2023

Related U.S. Application Data

(63) Continuation of application No. 17/491,968, filed on Oct. 1, 2021.

(60) Provisional application No. 63/086,583, filed on Oct. 1, 2020.

(51) Int. Cl.
*A61M 25/01* (2006.01)
*A61M 25/09* (2006.01)

(52) U.S. Cl.
CPC ............ *A61M 25/0152* (2013.01); *A61M 2025/09083* (2013.01); *A61M 2205/0266* (2013.01)

(58) Field of Classification Search
CPC .... A61M 25/0152; A61M 2025/09083; A61M 2205/0266
USPC ..................................................... 604/164.13
See application file for complete search history.

(56) References Cited

U.S. PATENT DOCUMENTS

| | | | |
|---|---|---|---|
| 3,906,938 | A | 9/1975 | Fleischhacker |
| 4,003,369 | A | 1/1977 | Heilman et al. |
| 4,080,706 | A | 3/1978 | Heilman et al. |
| 4,543,090 | A | 9/1985 | McCoy |
| 4,601,705 | A | 7/1986 | McCoy |
| 4,796,642 | A | 1/1989 | Harris |
| 4,834,709 | A | 5/1989 | Banning et al. |

(Continued)

FOREIGN PATENT DOCUMENTS

| | | |
|---|---|---|
| AU | 2013204243 A1 | 5/2013 |
| CN | 104887265 A | 9/2015 |

(Continued)

*Primary Examiner* — Phillip A Gray
(74) *Attorney, Agent, or Firm* — BakerHostetler

(57) ABSTRACT

An assembly is provided for accessing a superior vena cava of a patient without visualization of a vasculature of the patient. A stylet has an elongated body including a core wire disposed within a tubular body, the core wire having a pre-formed shape in a first state and a straightened shape in a second state. A first portion of the core wire has a substantially straight shape in the first state. A second portion of the core wire has a first pre-formed bend in the first state. A third portion of the core wire has a substantially straight shape in the first state. A fourth portion of the core wire has a second pre-formed bend in the first state. A fifth portion of the core wire has a substantially straight shape in the first state and includes a narrow segment that increases deflection of the distal tip.

21 Claims, 14 Drawing Sheets

(56) References Cited

U.S. PATENT DOCUMENTS

| | | | |
|---|---|---|---|
| 4,854,330 A | 8/1989 | Evans et al. |
| 4,905,698 A | 3/1990 | Strohl et al. |
| 4,925,445 A | 5/1990 | Sakamoto et al. |
| 5,078,678 A | 1/1992 | Katims |
| 5,099,845 A | 3/1992 | Besz et al. |
| 5,147,317 A | 9/1992 | Shank et al. |
| 5,230,348 A | 7/1993 | Shibe et al. |
| 5,299,580 A | 4/1994 | Atkinson et al. |
| 5,336,182 A | 8/1994 | Lundquist et al. |
| 5,365,942 A | 11/1994 | Shank |
| 5,395,327 A | 3/1995 | Lundquist et al. |
| 5,531,686 A | 7/1996 | Lundquist et al. |
| 5,606,981 A | 3/1997 | Tartacower et al. |
| 5,728,148 A | 3/1998 | Bostrom et al. |
| 5,807,339 A | 9/1998 | Bostroem et al. |
| 5,826,576 A | 10/1998 | West |
| 5,987,344 A | 11/1999 | West |
| 6,035,224 A | 3/2000 | West |
| 6,059,771 A | 5/2000 | Balbierz et al. |
| 6,156,027 A | 12/2000 | West |
| 6,169,916 B1 | 1/2001 | West |
| RE37,148 E | 4/2001 | Shank |
| 6,263,224 B1 | 7/2001 | West |
| 6,356,791 B1 | 3/2002 | Westlund et al. |
| 6,671,560 B2 | 12/2003 | Westlund et al. |
| 6,673,025 B1 | 1/2004 | Richardson et al. |
| 6,702,780 B1 | 3/2004 | Gilboa et al. |
| 6,770,038 B2 | 8/2004 | Balbierz et al. |
| 6,960,191 B2 | 11/2005 | Howlett et al. |
| 7,048,695 B1 | 5/2006 | Schwager |
| 7,089,065 B2 | 8/2006 | Westlund et al. |
| 7,169,118 B2 | 1/2007 | Reynolds et al. |
| 7,455,646 B2 | 11/2008 | Richardson et al. |
| 7,645,242 B1 | 1/2010 | Jalisi et al. |
| 7,717,864 B1 | 5/2010 | Grandfield et al. |
| 7,942,832 B2 | 5/2011 | Kanuka et al. |
| 7,959,601 B2 | 6/2011 | McDaniel et al. |
| 8,022,331 B2 | 9/2011 | Reynolds et al. |
| 8,057,405 B2 | 11/2011 | Jalisi et al. |
| 8,123,702 B2 | 2/2012 | Grandfield et al. |
| 8,226,577 B2 | 7/2012 | Jalisi et al. |
| 8,376,961 B2 | 2/2013 | Ayman et al. |
| 8,380,289 B2 | 2/2013 | Zellers et al. |
| 8,391,956 B2 | 3/2013 | Zellers et al. |
| 8,409,103 B2 | 4/2013 | Grunwald et al. |
| 8,478,382 B2 | 7/2013 | Burnside et al. |
| 8,597,193 B2 | 12/2013 | Grunwald et al. |
| 8,728,075 B2 | 5/2014 | Wu et al. |
| 8,784,336 B2 | 7/2014 | Bown et al. |
| 8,801,633 B2 | 8/2014 | Fox et al. |
| 8,849,382 B2 | 9/2014 | Cox et al. |
| 8,882,705 B2 | 11/2014 | McDaniel et al. |
| 8,965,490 B2 | 2/2015 | Lee et al. |
| 8,971,994 B2 | 3/2015 | Burnside et al. |
| 9,119,551 B2 | 9/2015 | Qi et al. |
| 9,198,600 B2 | 12/2015 | Grunwald et al. |
| 9,204,819 B2 | 12/2015 | Grunwald et al. |
| 9,339,207 B2 | 5/2016 | Grunwald et al. |
| 9,463,301 B2 | 10/2016 | Bukhman |
| 9,549,685 B2 | 1/2017 | Cox et al. |
| 9,649,048 B2 | 5/2017 | Cox et al. |
| 9,681,823 B2 | 6/2017 | Messerly et al. |
| 9,743,994 B2 | 8/2017 | Wenzel et al. |
| 9,901,714 B2 | 2/2018 | Lemon et al. |
| 9,999,371 B2 | 6/2018 | Messerly et al. |
| 9,999,750 B2 | 6/2018 | Bukhman |
| 10,004,875 B2 | 6/2018 | Bown et al. |
| 10,098,567 B2 | 10/2018 | Nelson et al. |
| 10,165,962 B2 | 1/2019 | Messerly et al. |
| 10,197,518 B2 | 2/2019 | Nelson et al. |
| 10,321,890 B2 | 6/2019 | Grunwald et al. |
| 10,335,240 B2 | 7/2019 | Grunwald et al. |
| 10,470,743 B2 | 11/2019 | Grunwald et al. |
| 10,480,959 B2 | 11/2019 | Nelson et al. |
| 10,722,686 B2 | 7/2020 | Bukhman |
| 10,751,509 B2 | 8/2020 | Misener |
| 10,849,695 B2 | 12/2020 | Cox et al. |
| 10,966,630 B2 | 4/2021 | Messerly et al. |
| 11,006,854 B2 | 5/2021 | Aman et al. |
| 11,027,101 B2 | 6/2021 | Lemon et al. |
| 11,122,991 B2 | 9/2021 | Nelson et al. |
| 11,150,207 B2 | 10/2021 | Nelson et al. |
| 11,207,496 B2 | 12/2021 | Rome et al. |
| 2002/0065486 A1 | 5/2002 | Balbierz et al. |
| 2002/0077686 A1 | 6/2002 | Westlund et al. |
| 2003/0144657 A1* | 7/2003 | Bowe ............... A61M 25/0147 606/41 |
| 2004/0102829 A1 | 5/2004 | Bonner et al. |
| 2004/0111059 A1 | 6/2004 | Howlett et al. |
| 2004/0167436 A1* | 8/2004 | Reynolds ............. A61M 25/09 600/585 |
| 2005/0027343 A1 | 2/2005 | Westlund et al. |
| 2006/0116576 A1 | 6/2006 | McGee et al. |
| 2006/0116609 A1 | 6/2006 | Kanuka et al. |
| 2006/0184106 A1 | 8/2006 | McDaniel et al. |
| 2006/0189959 A1 | 8/2006 | Schneiter |
| 2006/0276868 A1 | 12/2006 | Worley |
| 2007/0016068 A1 | 1/2007 | Grunwald et al. |
| 2007/0016069 A1 | 1/2007 | Grunwald et al. |
| 2007/0016070 A1 | 1/2007 | Grunwald et al. |
| 2007/0016072 A1 | 1/2007 | Grunwald et al. |
| 2007/0049846 A1 | 3/2007 | Bown et al. |
| 2007/0114211 A1 | 5/2007 | Reynolds et al. |
| 2007/0244413 A1 | 10/2007 | Biggins |
| 2008/0200879 A1 | 8/2008 | Jalisi et al. |
| 2008/0216826 A1 | 9/2008 | Boyden et al. |
| 2009/0005675 A1 | 1/2009 | Grunwald et al. |
| 2009/0024018 A1 | 1/2009 | Boyden et al. |
| 2009/0118612 A1 | 5/2009 | Grunwald et al. |
| 2009/0131913 A1 | 5/2009 | Grandfield et al. |
| 2009/0156926 A1 | 6/2009 | Messerly et al. |
| 2009/0177090 A1 | 7/2009 | Grunwald et al. |
| 2009/0234328 A1 | 9/2009 | Cox et al. |
| 2010/0004562 A1 | 1/2010 | Jalisi et al. |
| 2010/0004662 A1 | 1/2010 | Ollivier |
| 2010/0036227 A1 | 2/2010 | Cox et al. |
| 2010/0179562 A1 | 7/2010 | Linker et al. |
| 2010/0222664 A1 | 9/2010 | Lemon et al. |
| 2011/0218492 A1 | 9/2011 | McDaniel et al. |
| 2012/0130228 A1 | 5/2012 | Zellers et al. |
| 2012/0130229 A1 | 5/2012 | Zellers et al. |
| 2012/0136242 A1 | 5/2012 | Qi et al. |
| 2012/0220854 A1 | 8/2012 | Messerly et al. |
| 2013/0060116 A1 | 3/2013 | Messerly et al. |
| 2013/0245434 A1 | 9/2013 | Messerly et al. |
| 2013/0289417 A1 | 10/2013 | Grunwald et al. |
| 2013/0296725 A1 | 11/2013 | Lee et al. |
| 2014/0188133 A1 | 7/2014 | Misener |
| 2014/0249505 A1 | 9/2014 | Bukhman |
| 2014/0309624 A1 | 10/2014 | Bown et al. |
| 2015/0018701 A1 | 1/2015 | Cox et al. |
| 2015/0105721 A1 | 4/2015 | Osypka et al. |
| 2015/0320975 A1 | 11/2015 | Simpson et al. |
| 2016/0015933 A1 | 1/2016 | Bukhman |
| 2016/0143560 A1 | 5/2016 | Grunwald et al. |
| 2016/0151118 A1 | 6/2016 | Grunwald et al. |
| 2016/0228019 A1 | 8/2016 | Grunwald et al. |
| 2016/0245670 A1 | 8/2016 | Nelson et al. |
| 2016/0245766 A1 | 8/2016 | Nelson et al. |
| 2016/0256224 A1 | 9/2016 | Wenzel et al. |
| 2016/0320210 A1 | 11/2016 | Nelson et al. |
| 2017/0021131 A1 | 1/2017 | Bukhman |
| 2017/0035392 A1 | 2/2017 | Grunwald et al. |
| 2017/0215762 A1 | 8/2017 | Burnside et al. |
| 2017/0231700 A1 | 8/2017 | Cox et al. |
| 2017/0281029 A1 | 10/2017 | Messerly et al. |
| 2018/0092651 A1 | 4/2018 | Terashi et al. |
| 2018/0116551 A1 | 5/2018 | Newman et al. |
| 2018/0169389 A1 | 6/2018 | Lemon et al. |
| 2018/0242881 A1 | 8/2018 | Aman et al. |
| 2018/0296122 A1 | 10/2018 | Messerly et al. |
| 2018/0296796 A1 | 10/2018 | Bukhman |
| 2018/0304043 A1 | 10/2018 | Bown et al. |
| 2019/0086349 A1 | 3/2019 | Nelson et al. |

(56) References Cited

U.S. PATENT DOCUMENTS

| | | |
|---|---|---|
| 2019/0099108 A1 | 4/2019 | Messerly et al. |
| 2019/0150784 A1 | 5/2019 | Nelson et al. |
| 2020/0345427 A1 | 11/2020 | Victor |
| 2021/0077201 A1 | 3/2021 | Cox et al. |

FOREIGN PATENT DOCUMENTS

| | | |
|---|---|---|
| GB | 2064963 A | 6/1981 |
| JP | 56-101305 U | 8/1981 |
| JP | 09-173464 A | 7/1997 |
| JP | 2003-508168 A | 3/2003 |
| JP | 2003-284780 A | 10/2003 |
| JP | 2015-188528 A | 11/2015 |
| JP | 2015-535714 A | 12/2015 |
| WO | 2014/052894 A2 | 4/2014 |
| WO | 2018/005169 A1 | 1/2018 |
| WO | 2009/137262 A2 | 11/2019 |

\* cited by examiner

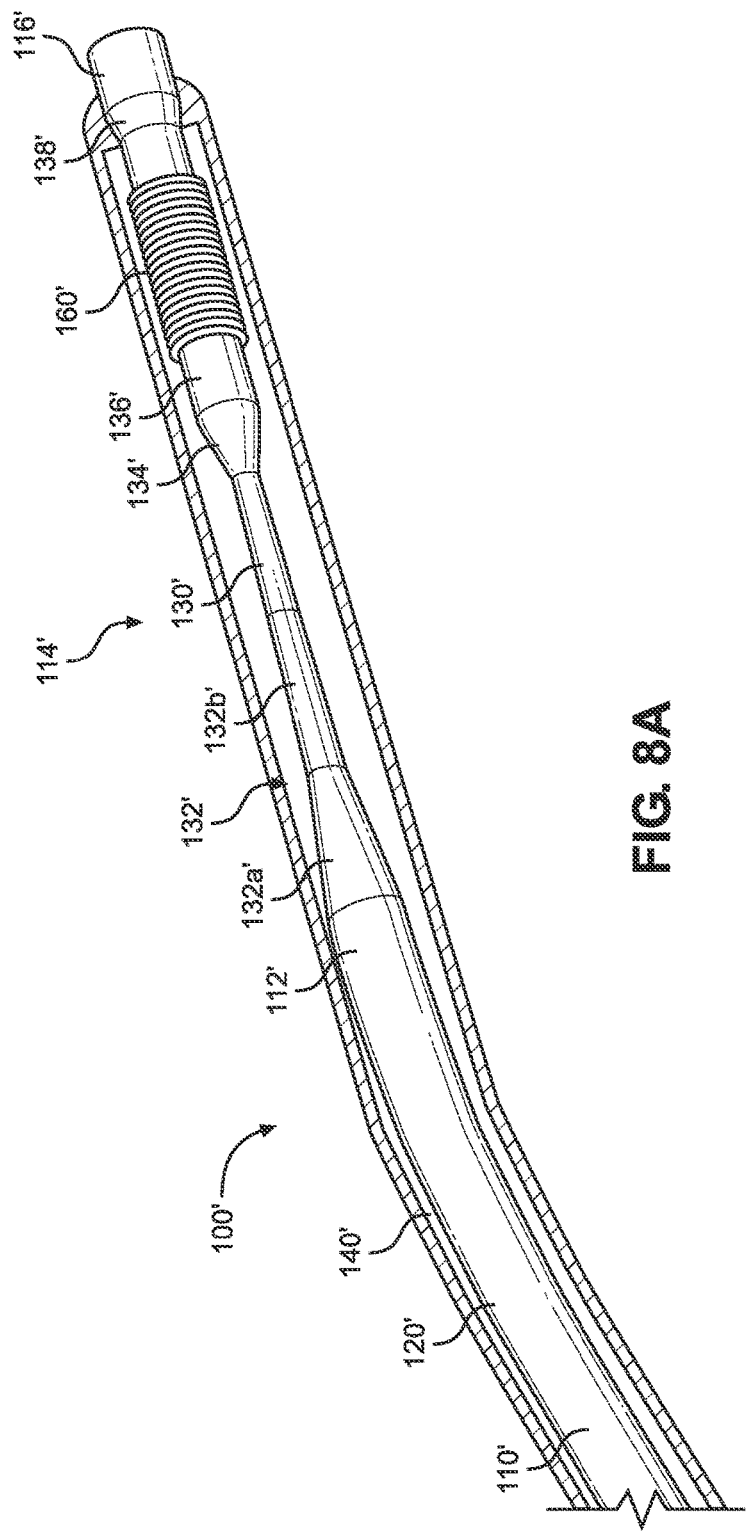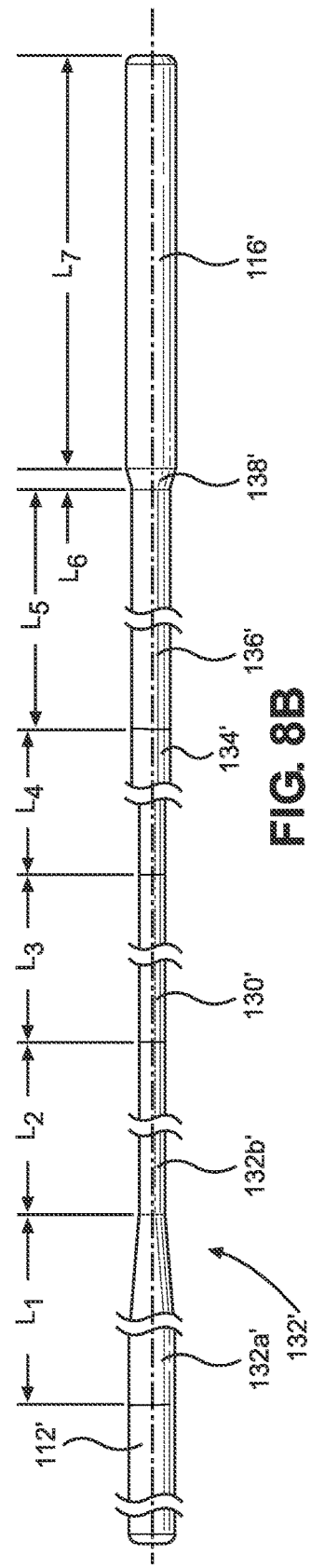
FIG. 8A
FIG. 8B

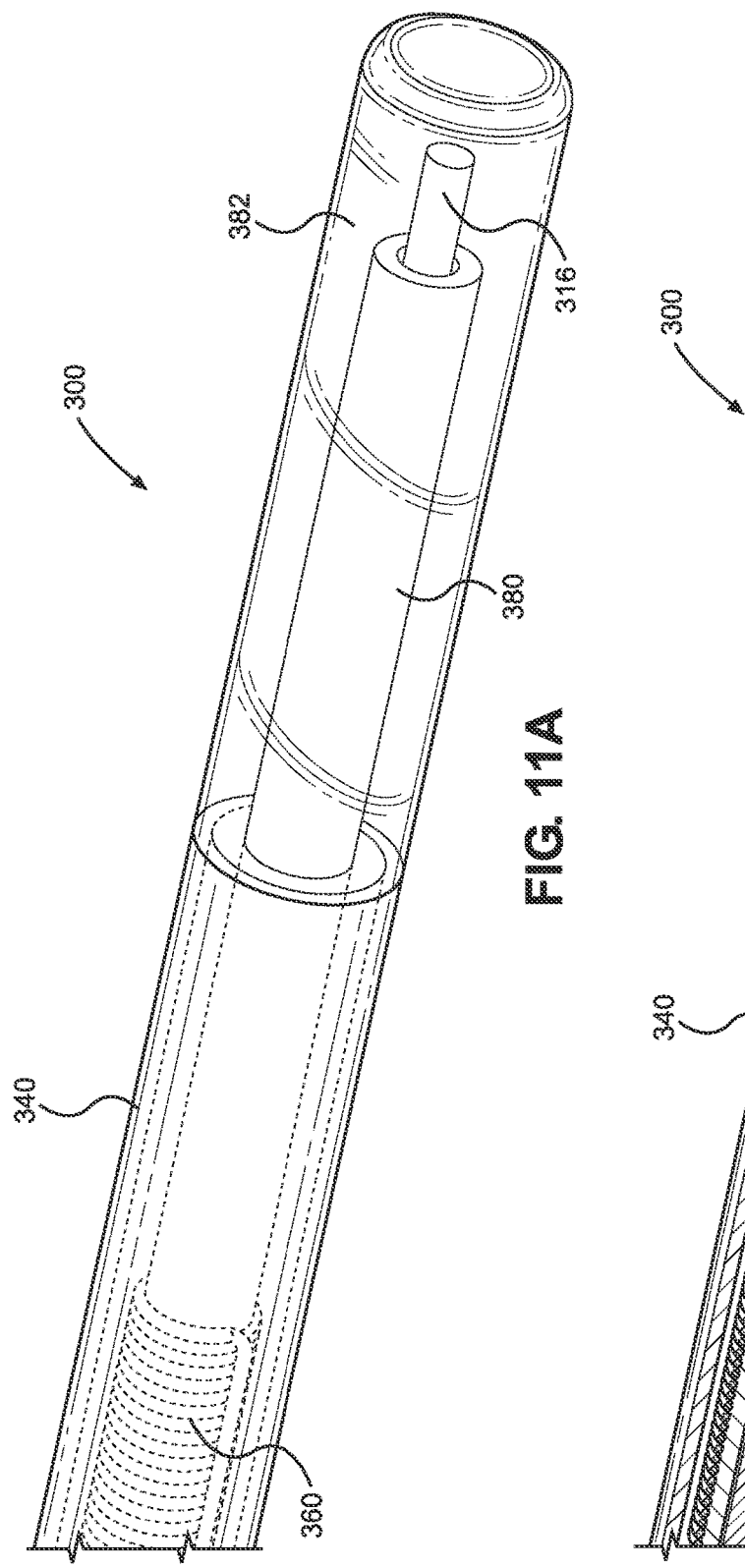
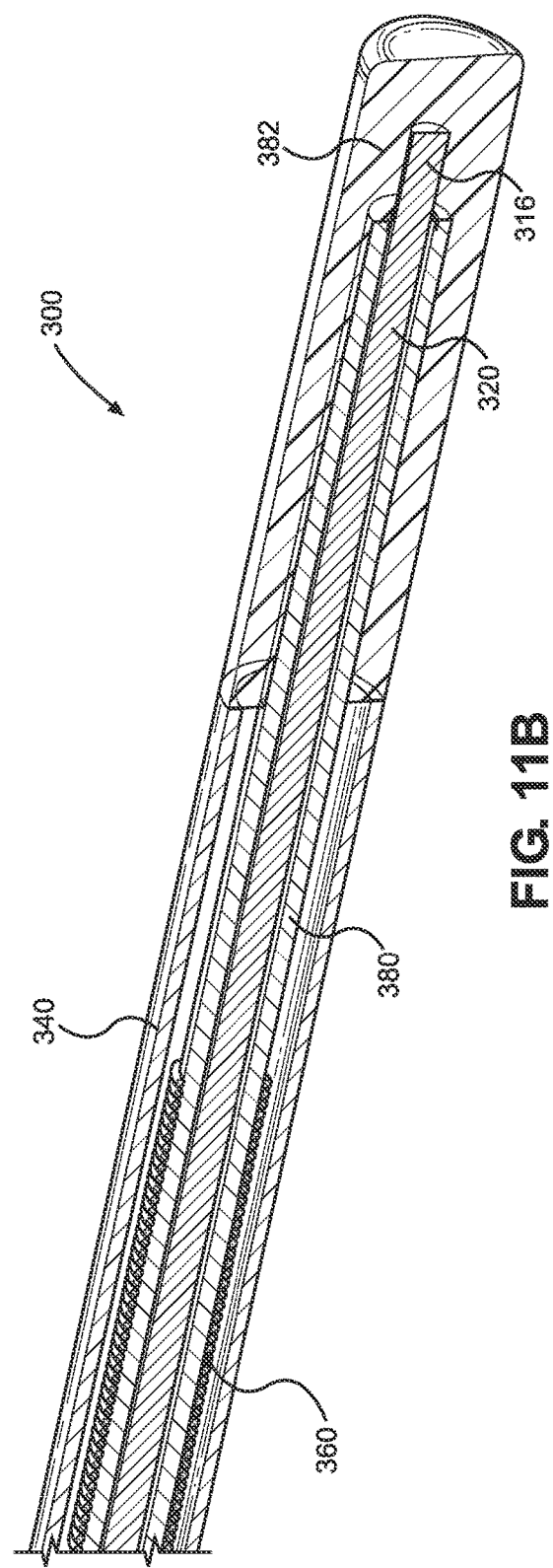

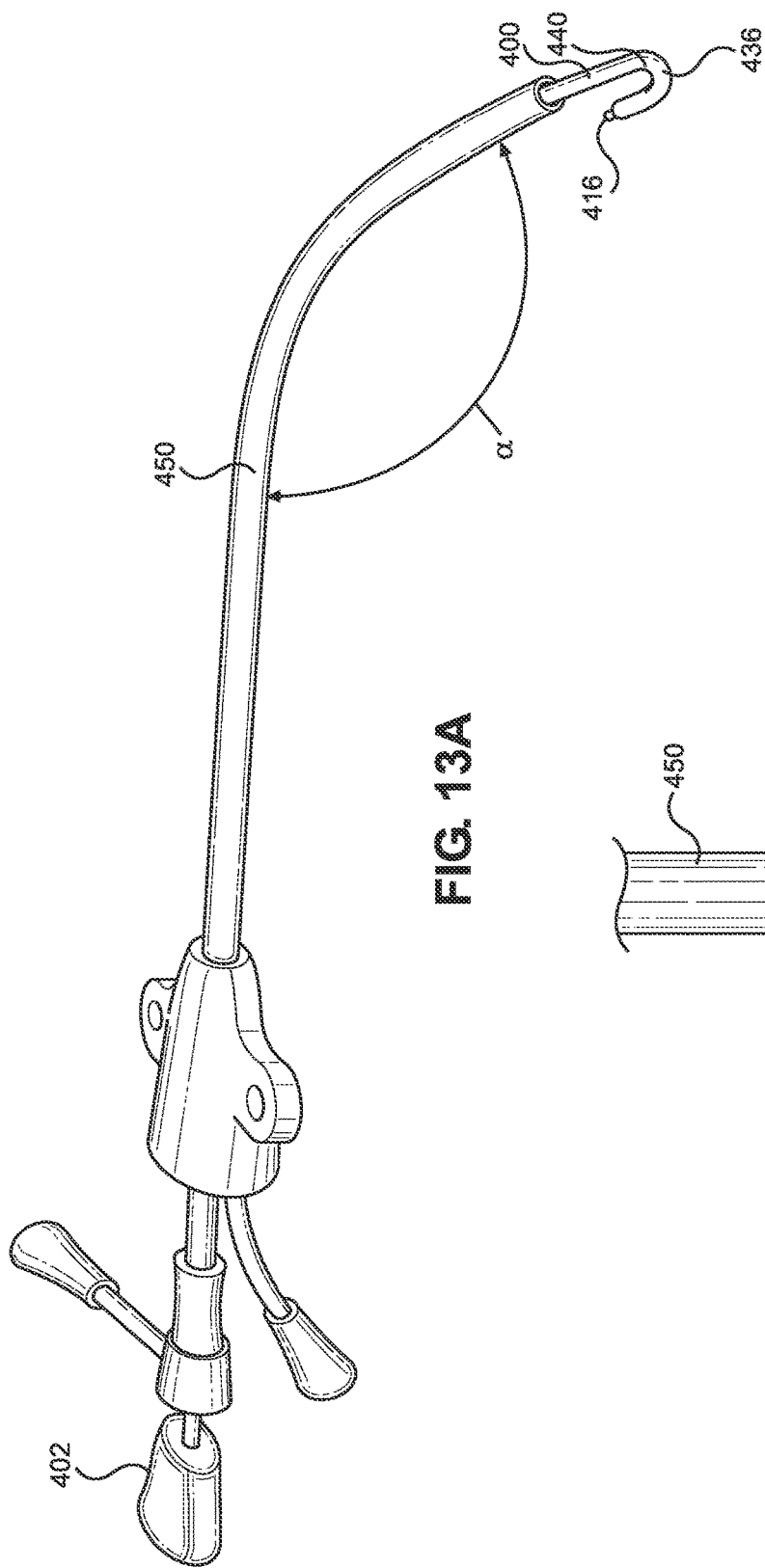
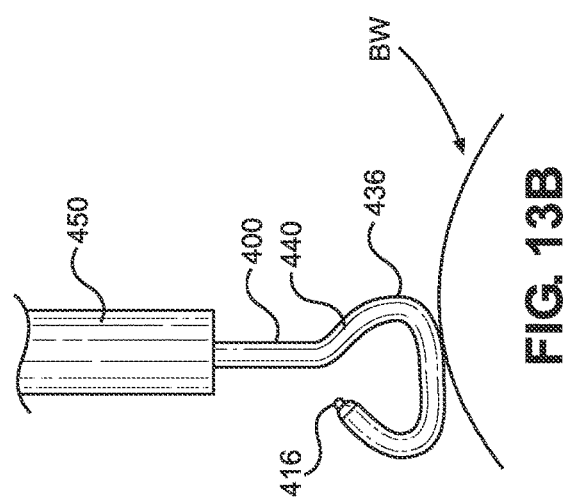

STYLET WITH IMPROVED THREADABILITY

PRIORITY

The present application is a continuation of U.S. patent application Ser. No. 17/491,968 filed on Oct. 1, 2021, which claims priority to U.S. Provisional Patent Application No. 63/086,583 filed on Oct. 1. 2020, the entire disclosures of which are expressly incorporated herein in their entirety.

TECHNICAL FIELD

The present disclosure relates generally to stiffening wires or stylets for placement of vascular catheters, and more particularly to low or non-torqueable stiffening wires or stylets with improved threadability.

BACKGROUND

A PICC (Peripherally Inserted Central Venous Catheter) is a catheter to be inserted into a vein of the upper arm and threaded to the Superior Vena Cava (SVC). The PICC provides access to the large central veins near the heart, generally to administer medications or liquid nutrients. The PICC can help avoid the pain of frequent needle sticks and reduce the risk of irritation to the smaller veins in your arms.

Overview

The present inventors recognize that there is a need to improve one or more features of the threadability of stylets, more specifically stylets to be assembled with a PICC. PICCs are often inserted at the bedside without sophisticated equipment for visualization of the anatomy. Some newer equipment is available that displays the location of the PICC on a monitor, but this equipment only provides an approximate reference for tip location relative to an external device. The distal tip of the stylet still often hits a wall of the vasculature prior to sharp curves, buckles, and does not advance forward, e.g., goes up other branches of veins that are not in the intended insertion pathway to the SVC, and/or contacts vein walls and loops back on itself. This may result in several attempts before the PICC is properly threaded into the SVC or may even prevent the user from being able to properly place the PICC at all. The patient may then need to be moved to another location of the hospital in order to visualize the anatomy with more sophisticated equipment for insertion of the PICC into the final location. The disclosed invention addresses one or more of these deficiencies and/or other deficiencies of the prior art.

Thus, a first aspect of the present invention is directed to a stylet having: a core wire including: a first pre-formed bend of a first angle; a second pre-formed bend of a second angle, the second pre-formed bend being distal of the first pre-formed bend, and the first angle being greater than the second angle; and a narrow segment being distal of the second-preformed bend and having a reduced width or diameter that increases deflection of a distal tip.

In some embodiments, the first angle is about 15-90° with respect to a longitudinal axis of the stylet, and an arc length of the first pre-formed bend is about 3-7 inches. In some embodiments, the second angle is about 8-15" with respect to a longitudinal axis of the stylet, and an arc length of the second pre-formed bend is about 0.2-0.5 inches. In some embodiments, the first pre-formed bend and the second pre-formed bend are entirely within 10 inches from an end of the distal tip of the core wire. In some embodiments, the first angle is about 60° with respect, to a longitudinal axis of the stylet, and the second angle is about 10° with respect to the longitudinal axis of the stylet. In some embodiments, the first pre-formed bend is longer than the second pre-formed bend. In some embodiments, the first pre-formed bend has an arc length of at least 4 inches longer than the second pre-formed bend. In some embodiments, the first pre-formed bend and the second pre-formed bend are in the same plane. In some embodiments, the narrow segment includes a rounded and/or flattened cross-section. In some embodiments, the core wire further includes a distal segment between the narrow segment and the distal tip, the distal segment having a width or diameter greater than the width or diameter of the narrow segment. In some embodiments, the distal tip has a width or diameter greater than the distal segment. In some embodiments, the core wire includes a proximal taper proximal of the narrow segment and a distal taper distal of the narrow segment. In some embodiments, the proximal taper is longer than the distal taper. In some embodiments, the proximal taper includes a first tapered portion and a second tapered portion, the first tapered portion being tapered at a greater angle than the second tapered portion. In some embodiments, the stylet further includes a tubular body disposed over the core wire. In some embodiments, the distal tip of the core wire extends distally of the tubular body, and the distal tip is conductive of an electrocardiogram (ECG) signal. In some embodiments, the tubular body has an opening in a sidewall to allow fluid contact with the core wire. In some embodiments, the stylet further includes a navigation device disposed over the core wire and within the tubular body. In some embodiments, the navigation device includes a conductive coil. In some embodiments, the stylet has minimal or no torquability. In some embodiments, the core wire further includes an intermediate portion of about 1-3 inches (about 2.5-7.5 cm) extending between the first pre-formed bend and the second pre-formed bend. In some embodiments, the core wire includes a distal portion encompassing the narrow segment, the distal portion extending about 1-2 inches (about 2.5-5 cm) from the second pre-formed bend to an end of the distal tip. In some embodiments, the stylet further includes a housing member at a proximal end of the core wire. In some embodiments, the core wire includes a nickel titanium alloy. In some embodiments, the distal tip is formed of one of a J-shape, a basket, or a mesh. In some embodiments, the stylet is a component of an assembly including a second stylet that is conductive of an ECG signal. In some embodiments, the stylet is a component of an assembly including a catheter.

A second aspect of the present invention is directed to a low or non-torqueable, stylet having: a core wire including: a first pre-formed bend of a first angle of about 15-90°; a second pre-formed bend of a second angle of about 8-15°, the second preformed bend being distal of the first preformed bend, and the first pre-formed bend being longer than the second pre-formed bend; an intermediate portion of about 1-3 inches (about 2.5-7.5 cm) extending between the first pre-formed bend and the second pre-formed bend; and a distal portion extending about 1-2 inches (about 2.5-5 cm) between the second pre-formed bend and an end of a distal tip, the distal portion having a section of reduced width or diameter that increases deflection of the distal tip; a tubular body disposed around the core wire; and a navigation device disposed around the core wire and within the tubular body.

A third aspect of the present invention is directed to a stylet having a distal portion with a narrow segment, a proximal taper proximal of the narrow segment, and a distal taper distal of the narrow segment, wherein a length of the proximal taper is greater than a length of the distal taper. In some embodiments, the length of the proximal taper is at least twice the length of the distal taper. In some embodiments, the length of the proximal taper is less than about six times the length of the distal taper. In some embodiments, the proximal taper includes a first tapered portion and a second tapered portion, the first tapered portion being tapered at a greater angle than the second tapered portion. In some embodiments, the first tapered portion is proximal of the second tapered portion. In some embodiments, the stylet includes: a second distal taper distal of the narrow segment, and a distal segment extending between the distal taper and the second distal taper. In some embodiment, the stylet further includes a navigation device disposed over the distal segment. In some embodiments, a length from the proximal end of the narrow segment to a distal end of the stylet is less than or equal to about 1.6 inches (less than about 4 centimeters). In some embodiments, a length of the narrow segment is greater than a length of the distal taper. In some embodiments, the length of the narrow segment is greater than the length of the proximal taper. In some embodiments, the narrow segment has a constant width or diameter. In some embodiments, a width or diameter of a distal tip of the stylet is substantially the same as a width or diameter of a proximal portion of the stylet. In some embodiments, the distal tip includes a rounded and/or tapered edge. In some embodiments, the stylet has a preformed straight configuration. In some embodiments, the stylet has a pre-formed curved configuration.

BRIEF DESCRIPTION OF THE DRAWINGS

In order that the invention may be readily understood, aspects of this invention are illustrated by way of examples in the accompanying drawings.

FIG. 8A-B illustrate views of a second embodiment of a stylet according to the present invention.

FIGS. 11A-B illustrate views of a fifth embodiment of the stylet according to the present invention.

FIG. 13A illustrates an isometric view of a sixth embodiment of a stylet in a catheter according to the present invention.

FIG. 13B illustrates a distal end of the stylet and catheter of FIG. 13A.

The same reference numbers are used in the drawings and the following detailed description to refer to the same or similar parts.

DETAILED DESCRIPTION

The present invention is generally directed to a stylet providing a specific combination of bend and/or stiffness profiles that enables a catheter to be consistently threaded through anatomical curves of the vasculature into a desired location of the vasculature. The stylet of the present invention may be low or non-torqueable and allow the user to thread the stylet without needing to know the distal tip orientation (i.e., the direction the tip is pointing, "up" or "down") or control the distal tip orientation by rotating the proximal end of the stylet. More specifically, the stylet may provide a consistently favorable approach angle through the vasculature at a confluence of the internal jugular vein, brachiocephalic vein, and/or subclavian vein) into the desired location. This approach angle may be favorable regardless of how the user inserts the catheter into the vasculature and/or rotates the proximal end of the catheter during threading. The stylet may further have a narrow segment that is more flexible or floppier than the other portions of the stylet. The floppiness of the narrow segment may enhance the deflection of the distal tip when contacting a vein wall to reduce vessel trauma. Furthermore, the narrow segment may improve the contact angle of the distal tip by bowing upward when the distal tip contacts the vein wall, such the distal tip points downward in a favorable direction. Commercial benefits include fewer insertion attempts, less insertion time, and reduced user frustration during insertion.

Figure 1:
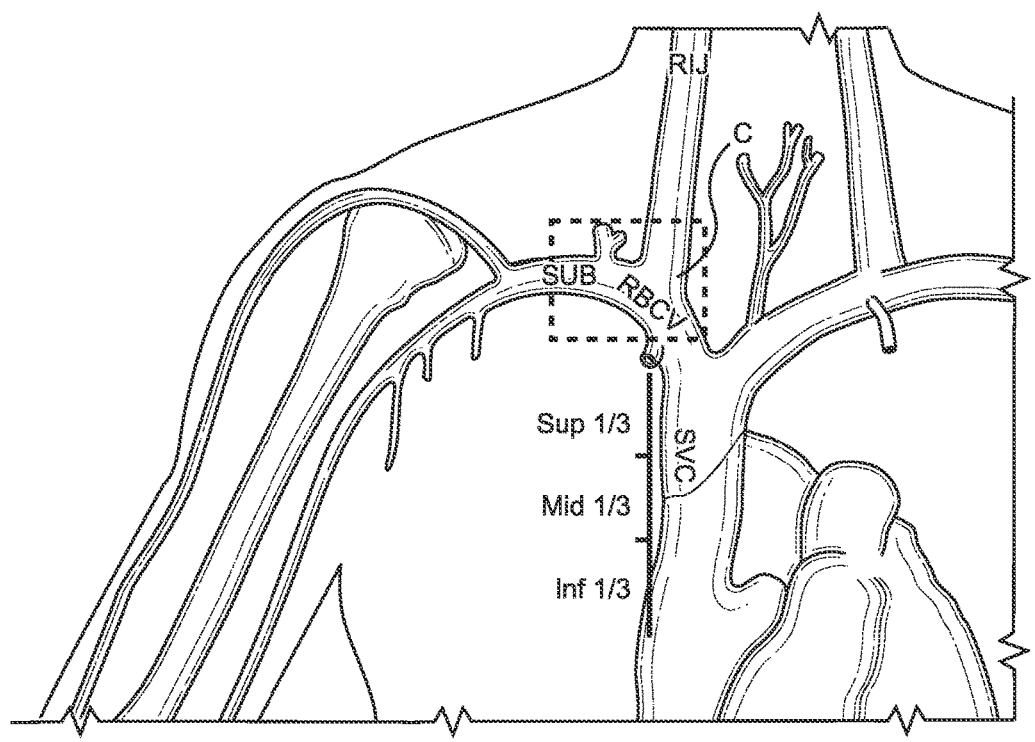
FIG. 1 illustrates vasculature of a human body.

FIG. 1 illustrates a reference anatomical graphic that includes vasculature of a potential pathway through which a stylet assembled with a catheter (e.g., a peripherally inserted central venous catheter, PICC) can be threaded to the superior vena cava (SVC), according to the present invention. The stylet/PICC may enter the vasculature at a number of different venous locations (e.g., the basilic, brachial, or cephalic vein). A needle puncture may access the vasculature at the venous location of choice, an access wire may be inserted through the needle into the vasculature, a sheath may be guided over the access wire after the needle is removed. After the access wire is removed from the sheath, the stylet/PICC may then be threaded through the sheath entering the vasculature at the venous location of choice, into and through a subclavian vein (SUB), into and through a brachiocephalic vein (BCV, e.g., the right brachiocephalic vein, RBCV), and ultimately into the SVC. The most common area for insertion difficulty is the area of a confluence (C) where the SUB ends and joins the internal jugular vein (IJ) and a BCV, as further illustrated in FIG. 6. The confluence (C) typically contains the sharpest curve in the anatomical pathway which may define a 90° curve or drop.

Due to this sharp curve, the catheter may deflect the wrong way (e.g., up the IJ) or get caught and not be able to be advanced at all. Although FIG. 1 and corresponding discussion is directed to insertion of the stylet through the SUB into the RBCV, the stylet of the present invention may be inserted through other pathways including through the left brachiocephalic vein (LBCV).

Figure 2:
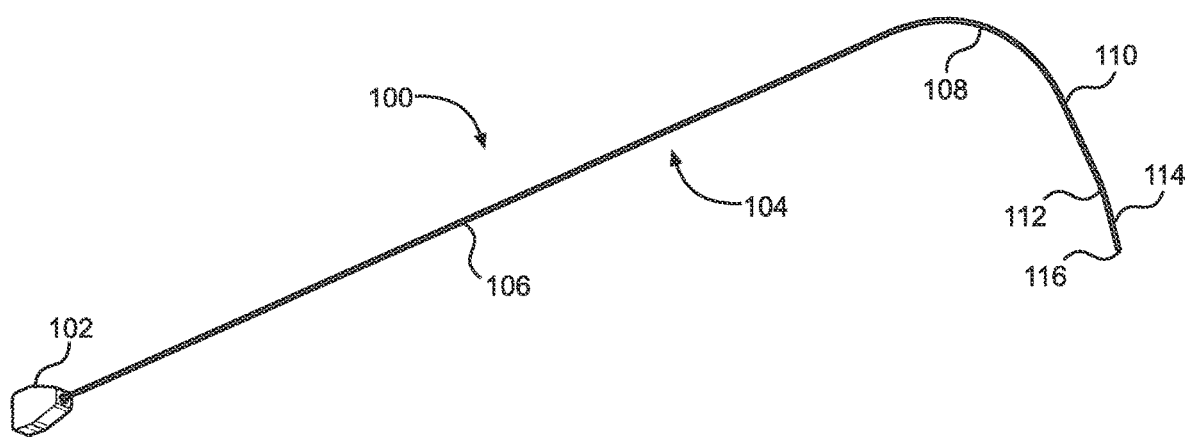
FIG. 2 illustrates a perspective view of a first embodiment of a stylet according to the present invention.
Figure 3:
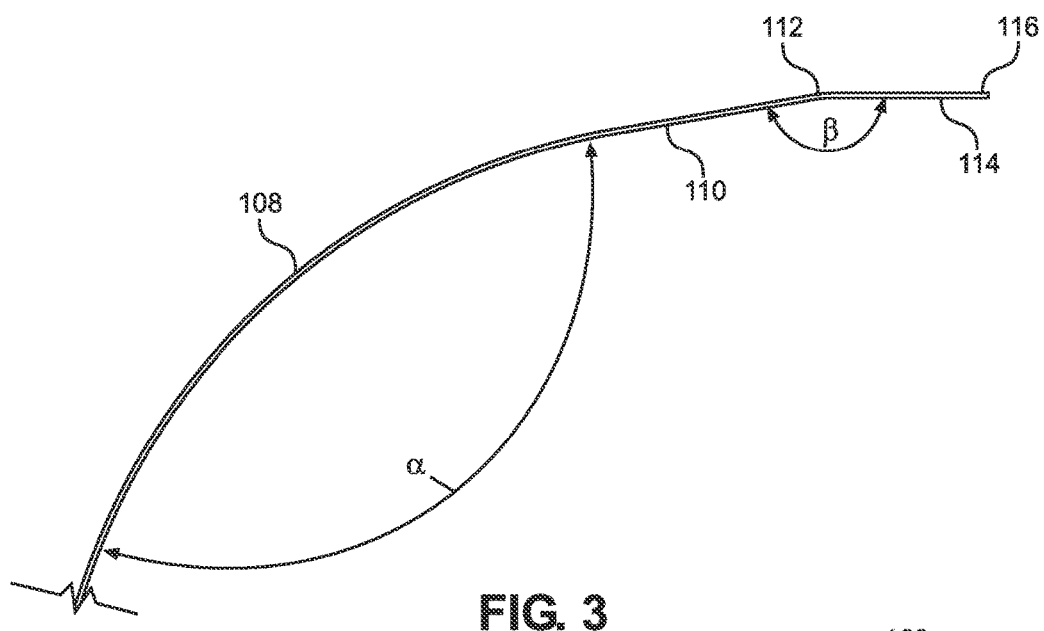
FIG. 3 illustrates a side view of a distal portion of the stylet of FIG. 2.
Figure 4:
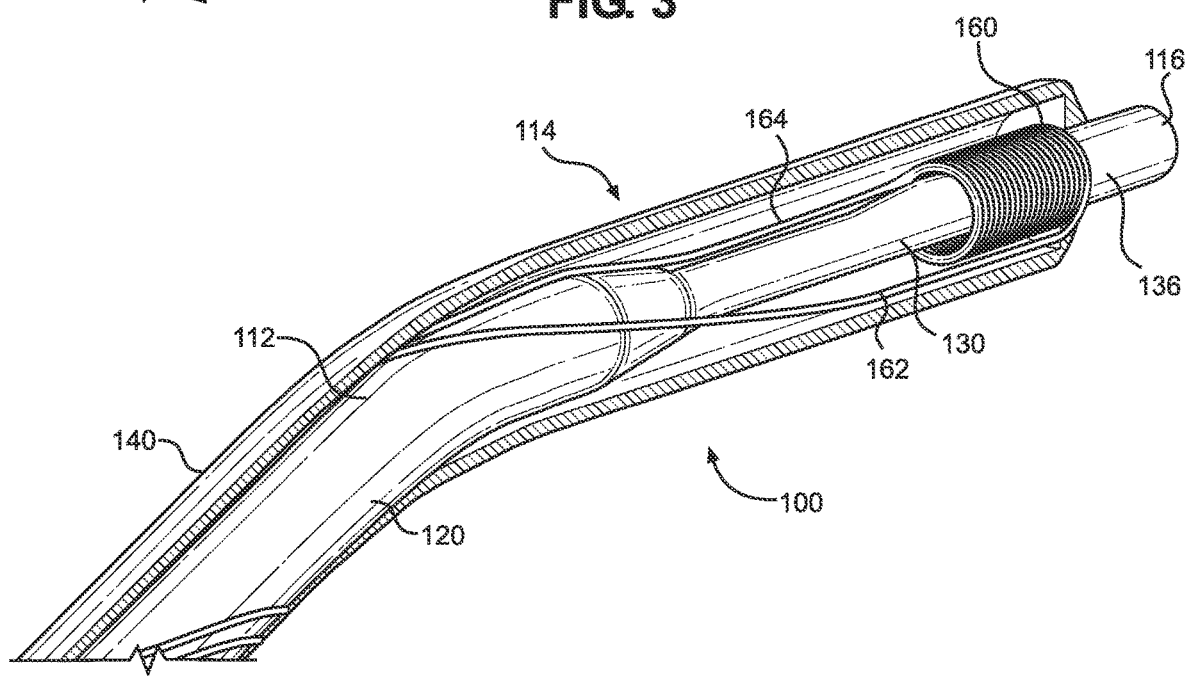
FIG. 4 illustrates a perspective view of the distal portion of a core wire and a tubular body of the stylet of FIGS. 2-3.
Figure 5:
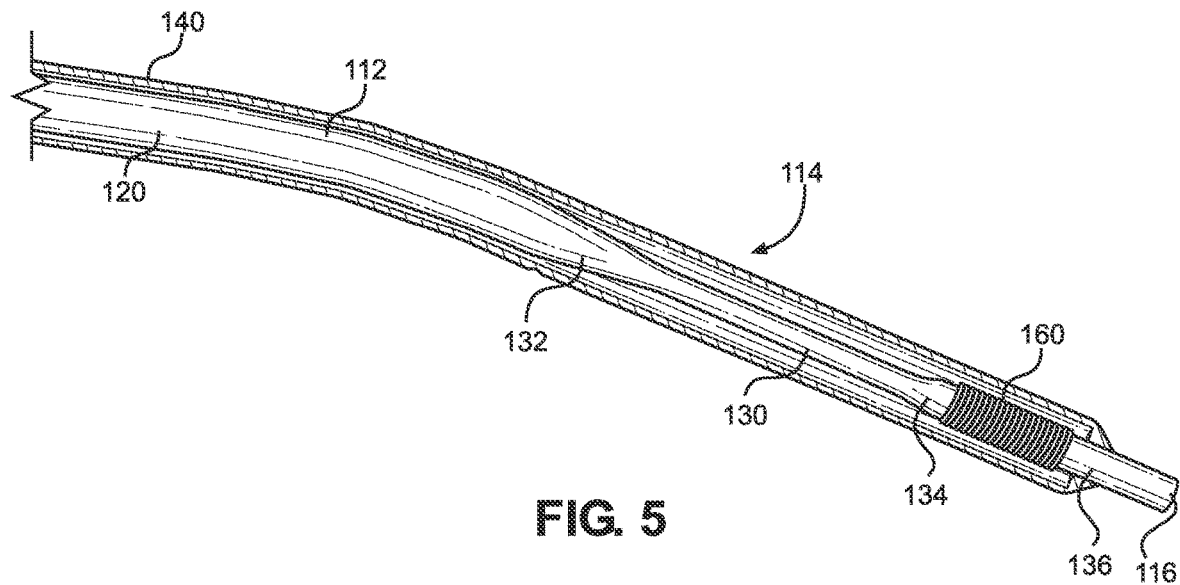
FIG. 5 illustrates a side view of the distal portion of the core wire and the tubular body of the stylet of FIGS. 2-4.
Figure 6:
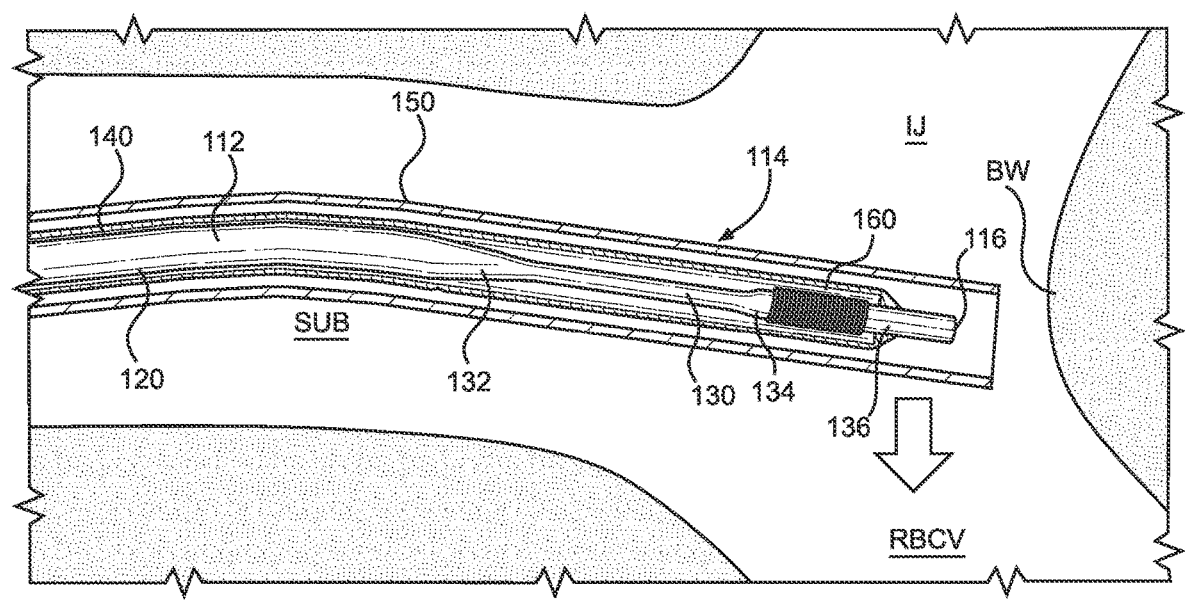
FIG. 6 illustrates the distal portion of the stylet of FIGS. 2-5 in a catheter being threaded through the vasculature of the human body of FIG. 1.

FIG. 2 illustrates an isometric view of a stylet 100 according to the present invention, and FIG. 3 illustrates a side view of a distal end of the stylet 100. As illustrated, the stylet 100 may include a housing member 102 at a proximal end of an elongated body 104 configured to he inserted through the vasculature. The elongated body 104 may include a core wire 120 and a tubular body 140 disposed around the core wire 120, as illustrated in FIGS. 4-6.

The core wire 120 may have a nominal or pre-formed shape as illustrated in FIGS. 2 and 3, including a preformed first curve or bend α ("body bend"). During insertion, the first bend α may be forced to elastically straighten due to the anatomical insertion pathway that is straighter than the pre-formed core wire. The core wire 120, when straightened, is in a slate of high potential energy and will try to compress back to its nominal shape to a state of lower potential energy, akin to a stretched spring trying to return to its original unstressed condition. When the distal tip 116 reaches the confluence (C), the lowest potential energy state of the first bend α forces the distal tip 116 to point down towards the SVC. The nominal shape and rigidity of the elongated body 104 may be formed by the pre-formed shape and rigidity of the core wire 120. As illustrated, the core wire 120 (and elongated body 104) may have a first portion 106 that is substantially straight in the nominal state and extends distally from the housing member 102. The core wire 120 (and elongated body 104) may have a second portion 108 that has the pre-formed first curve or bend α and extends distally from the first portion 106. The core wire 120 (and elongated body 104) may have a third portion (or intermediate portion) 110 that is substantially straight in the nominal state and extends distally from the second portion 108. The core wire 120 (and elongated body 104) may have a fourth portion 112 that has a pre-formed second curve or bend β and extends distally from the third portion 110. The core wire 120 (and elongated body 104) may have a fifth portion (or distal portion) 114 that is substantially straight in the nominal state and extends distally from the fourth portion 112 to the distal tip 116. Thus, the first bend α may be proximal of the second bend β and be spaced apart by the third portion 110. As further illustrated in FIG. 3, the first bend α may define a first angle of about 15-90° (e.g., 55-70°) between a longitudinal axis of each of the first and third portions 106, 110, thus the first bend α may define a supplementary arc (as illustrated in FIG. 3) of about 90-165° (however, the angle of the first bend α is defined herein between the longitudinal axis of each of the first and third portions 106, 110, unless otherwise indicated). The second bend β may define a second angle of about 8-15" between a longitudinal axis of the third and fifth portions 110, 114, thus the second bend β may define a supplementary arc (as illustrated in FIG. 3) of about 165-172° (however, the angle of the second bend β is defined herein between the longitudinal axis of each of the third and fifth portions 110, 114, unless otherwise indicated). The angles of the first bend α and second bend β may vary depending on the stiffness of a catheter (e.g., a PICC) 150 disposed around the stylet 100. In other words, the catheter 150 may nominally be straighter and have some stiffness, thus it may straighten out the stylet 100 at the first bend α and second bend β. The stiffness of the catheter 150 may depend on the brand, material, lumen, and size. For a stiffer catheter 150, the stylet 100 may be more curved to induce a proper angle for the vasculature. Thus, the stylet 100 may be designed to produce an assembly of the stylet 100 and catheter 150 with a first portion at the first bend α, having an angle of 5-80° and a second portion at the second bend β having an angle of 3-10°, each relative to the longitudinal axis of the assembly. Thus, the assembly of the stylet 100 and the catheter 150 is of a greater angle than the anatomical reference curvature.

The second portion 108 may have an arc length of about 3-7 inches (about 7.5-17.5 cm), e.g., about 5.3 inches (about 13.5 cm), the third portion 110 may have a length of about 0-3 inches (about 0-7.5 cm), the fourth portion 112 may have an arc length of about 0.2-0.5 inches (about 0.5-1.25 cm), and the fifth portion 114 may have a length of about 1-2 inches (about 2.5-5 cm). Thus, in a favorable embodiment for inserting a PICC, the first bend α may be a gradual bend at a first angle of about 60° starting about 3 inches (about 7.5 cm) from the end of the distal tip 116 and extending proximally to about 8.3 inches (about 21 cm) from the end of the distal tip 116. The second bend β may form a second angle of about 10°, for example, by bending the stylet 100 around a pin of about 0.25 inch (about 0.5 cm) diameter positioned about 1.2.5 inch (about 3 cm) from the end of the distal tip 116 and forming an arc length of about 0.22 inch (about 0.5 cm).

Therefore, the first angle of the first bend α (between the first and third portions 106, 108) may be substantially greater than the second angle of the second bend β (between third and fifth portions 110, 114). For example, the difference between the first angle of the first bend α and the second angle of the second bend β may be at least 40°. Furthermore, the arc length of the second portion 108 (and first bend α) may be substantially greater than the arc length of the fourth portion 112 (and second bend β). For example, the difference between the arc length of the second portion 108 (and first bend α) and the arc length of the fourth portion 112 (and second bend β) may be at least 4 inches (about 10 cm), and the first bend α and the second bend β may entirely be within 10 inches (25 cm) of the distal tip 116. Thus, the second bend β may have a proximity to the distal tip 116 such that when the distal tip 116 is at the confluence (C), the second bend β is in an area of reference anatomy (upstream of/towards the insertion site) that contains some curvature.

The first bend α may correspond to a body curve and the second bend β may correspond to a tip curve, and the first and second bends α, β may be in the same plane and same direction (to prevent counteracting of the bends α, β). The first bend α may be configured to self-orient the stylet 100 in the anatomy, and the second bend β may be configured for the distal tip 116 to approach the difficult curve locations of the anatomy at a favorable angle when the first bend α is self-oriented. Thus, the first and second bends α, β may increase the user's ability to thread the stylet 100 into the desired position, without visualization of the vessel or steering the stylet 100. For example, as illustrated in FIG. 6, the first and second bends α, β may be configured to automatically keep the distal tip 116 at an approach angle directed toward a lower portion of a back wall (BW) of the vasculature increasing the chance that the distal tip 116 points down towards the SVC. Additionally, the angle of the distal tip 116 reduces the chances that the distal tip 116 hits normal to the back wall ensuring that the distal tip 116 bows in a predictable direction and does not start to loop back onto itself or "tent". Furthermore, the distal tip 116 hitting at the favorable angle may cause the distal tip 116 to glance off the back wall (BW) of the vein and thread in the right direction down the RBVC without the user encountering too much resistance and therefore reducing trauma to the back wall (BW).

The style 100 may be self-orienting in that manual rotation of the proximal housing member 102 does not substantially transmit torque to the distal tip 116 enough to cause a consistent rotation. Thus, the core wire 120 may be low or non-torqueable. For example, the user may rotate the proximal housing member 102 a number of times before there is significant rotational movement translated to the distal tip 116, then the distal tip 116 may axially rotate around fully and quickly, and go back to a favorable location.

Thus, the first bend α may be configured to automatically align the stylet 100 with the curvature of the vasculature during insertion in order for the distal tip 116 to point "down" into the RBVC since the first and second bends α, β are in the same plane and same direction. The distal tip 116 may always points down when the distal tip 116 enters, for example, the confluence (C) of the vessels where PICCs have the most difficulty in navigating through the tight curvature. The stylet 100 may be non-torqueable and non-steerable removing control of the orientation of the distal tip 116 from the user and enabling the stylet 100 to automatically find the correct orientation in the vasculature no matter what orientation the stylet 100 is initially inserted and/or how the stylet 100 is rotated during insertion. Furthermore, in some embodiments, the stylet 100 may include a torque-limiting member on a proximal end of the core wire 120 that further reduces the ability of the user to transmit torque (e.g., a torque limiting ground section).

As further illustrated in FIGS. 4-6, the fifth portion 114 (including the distal tip 116) may have a narrow segment 130 that is more flexible or floppier than at least one or all of the proximal portions 106-112 of the stylet. The floppiness of the distal tip 116 may allow the distal tip 116 to deflect when contacting a vein wall without causing vessel trauma. Furthermore, the narrow segment 130 may improve the contact angle of the distal tip 116 by bowing upward when the distal tip 116 contacts the vein wall, such that, the distal tip 116 points downward toward the RBCV. The narrow segment 130 may be straight and have a constant width or diameter. The fifth portion 114 may have a short length to provide favorable deflection mechanics. The proximal portions 106-112 of the core wire 120 need to have sufficient stiffness (greater than the narrow segment 130) such that the shape of the core wire 120 influences the stylet 100 after assembly and the stylet 100 does not buckle too easily during insertion. Thus, the stylet 100 has a stiffness profile such that the narrow segment 130 of the fifth portion 114 may be the first location along the length of the core wire 120 to buckle which may improve the insertion angle of the distal tip 116 and maintain pushability of the assembly. If the proximal portions 106-112 of the core wire 120 buckle prior to the narrow segment 130 of the fifth portion 114, any longitudinal pushing force applied by the user may no longer transmitted to the distal tip 116 preventing the stylet 100 from advancing forward.

The narrow segment 130 of the fifth portion 114 may have a reduced width or diameter and be formed by a proximal taper 132 at a proximal end reducing the width or diameter of the stylet 100 from the fourth portion 112 and/or a distal taper 134 at a distal end increasing the width or diameter of the stylet 100 to a distal segment 136. The narrow segment 130 may have a rounded and/or flattened cross-section. Thus, the distal taper 134 may connect the narrow segment 130 to the distal segment 136, which connects to the distal tip 116. In some embodiments, the distal segment 136 and the distal tip 116 may have a width or diameter greater than a width or diameter of the narrow segment 130 and less than a width or diameter of the at least one of the portions 106-112 (e.g., the remainder of the core wire 120). For example, the portions 106-112 may have a width or diameter of about 0.011 inches (about 0.3 mm), the distal segment 136 and the distal tip 116 may have a width or diameter of about 0.007 inches (about 0.2 mm), and the narrow segment 130 may have a width or diameter of about 0.004 inches (about 0.1 mm). The proximal taper 132 may have a longer length and a more gradual slope than the distal taper 134, allowing the proximal taper 132 to withstand greater forces during insertion and prevent stress concentrations/weak points compromising the strength/performance of the stylet 100. For example, the proximal taper 132 may be at least about twice the length of the distal taper 134 and less than about six times the length of the distal taper 134 (e.g., at least three, four, or five times the length of the distal taper 134). Furthermore, a length between the proximal end of the narrow segment 130° and the distal tip of the stylet 100° may be less than or equal to about 1.6 inches, e.g. about 0.6-1.4 inches (less than or equal to about 4 cm, e.g., about 1.5-3.5 cm) to provide favorable deflection mechanics.

A conductive coil 160 may be disposed over and around the distal segment 136 of the core wire 120 to provide passive sensor coil capabilities for navigation. As illustrated in FIG. 4 (and omitted in FIGS. 2-3 for clarity), a first lead 162 may integrally connect to a distal end of the conductive coil 160, wrap around the core wire 120 (e.g., 5 times), and electrically connect to a circuit board (not shown) inside the housing member 102. Similarly, a second lead 164 may integrally connect to a proximal end of the conductive coil 160, wrap around the core wire 120 (e.g., 5 times), and electrically connect to the circuit board inside the housing member 102. The conductive coil 160 and leads 162, 164 may each be a conductive copper wire. In use, the conductive coil 160 may pick up electromagnetic signals generated and transmitted by one or more drive coils (not shown) external of the body. The resultant signal of the conductive coil 160 may be transmitted via at least one of the leads 162, 164 to the circuit board in the housing member 102. The circuit board may transmit the signal to a computer (not shown) to display a location of the fifth portion 114. Further discussion of the structure and function of the conductive coil 160 and tip navigation systems may be found in U.S. Pat. No. 10,098,567, the entire disclosure of which is incorporated herein by reference.

The tubular body 140 may be disposed over the core wire 120 and enclose the conductive coil 160 and leads 162, 164. The tubular body 140 may secure the leads 162, 164 and prevent the leads 162, 164 from coming loose and/or contacting fluid during insertion. The tubular body 140 may be made of a soft and flexible polymer (e.g., polyimide or nylon), not having a significant function or impact on the bend profile of the stylet 100. The tubular body 140 may include a lubricious coating or outer layer to decrease frictional forces between the catheter 150 to facilitate removal of the stylet 100. For example, the tubular body 140 may include a polytetrafluorethylene (PTFE) outer layer or a hydrophilic coating. The tubular body 140 may have a variation in frictional properties along its length, such that a distal portion of the tubular body 140 is more lubricous that a proximal portion of the tubular body 140. In some embodiments, the frictional variation may be provided by increased surface texture, with the distal portion of the tubular body being smoother than the proximal portion of the tubular body, and/or the proximal portion being more textured, roughened, or ribbed. The distal end of the tubular body 140 may be bonded to the core wire 120 distal of the conductive coil 160. For example, the distal end of the tubular body 140 may be bonded and/or sealed with a Cyanoacrylate adhesive to the core wire 120 to prevent fluid from entering the tubular body 140. In some embodiments, the tubular body 140 may include markings for the user to be able to visualize when the stylet 100 is sliding (intentionally and unintentionally) relative to the catheter 150.

The distal tip 116 formed by the core wire 120 may extend distally from the distal end of tubular body 140, and the distal tip 116 may be atraumatic (e.g., rounded and/or tapered edges) to reduce trauma on the vascular tissue. The distal tip 116 may be exposed to ensure adequate conduction of Electrocardiogram (ECG) signals that assist in determining proper positioning in the SVC. The ECG signals may be further conducted along the length of core wire 120 to the circuit board (not shown) inside the housing member 102. The. ECG conductivity and position determination are further discussed in U.S. Pat. No. 10,321,890, the entire disclosure of which is incorporated herein by reference.

Figure 7:
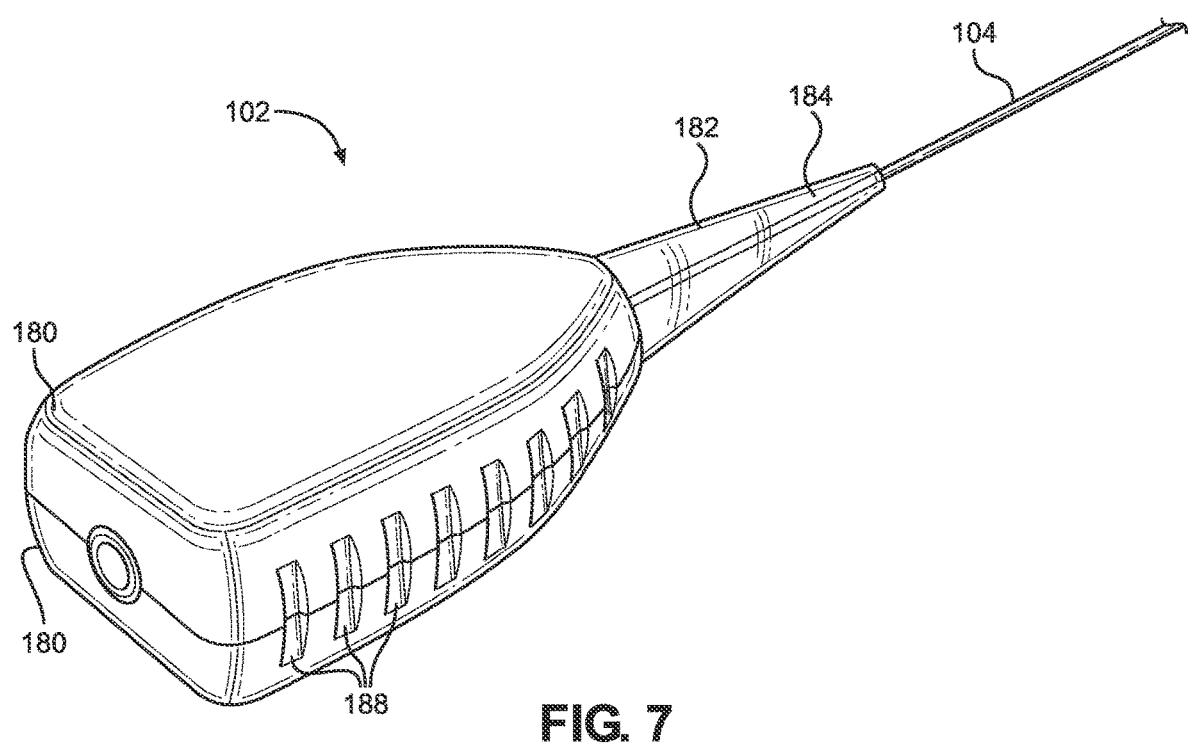
FIG. 7 illustrates an isometric view of a housing member of the stylet of FIGS. 1-6.

FIG. 7 illustrates an isometric view of the housing member 102. As illustrated, the housing member 102 may include first and second housing portions 180 and a nose member 182. The first and second housing portions 180 may be assembled to house electronic components (e.g., the circuit board) connected to the conductive coil 160 via the leads 162, 164. For example, the first and second portions 180 may have corresponding pins and holes configured to press together to form the housing member 102. Each of the first and second housing portions 180 may include grooves 188 on side surfaces that join to provide enhanced grip of the user. Each of the first and second housing portions 180 may also include protruding walls to be received in a neck or groove of the nose member 182 to secure the nose member 182 to the housing member 102 when assembled. The nose member 182 may define a sleeve having a lumen therethrough to receive the elongated body 104 into the housing member 102. The nose member 182 may have a tapered distal portion 184 extending distally from the first and second housing portions 180 and a proximal portion received between the first and second housing portions 180. The nose member 182 may be made of an elastomeric material (e.g., silicone rubber) to provide strain relief for the attachment of the elongated body 104 to the housing 102.

FIGS. 8A-B illustrate a stylet 100' according to a second embodiment of the present invention. The stylet 100' may have similar features as discussed above with reference to the stylet 100 and incorporated herein (unless otherwise indicated), including the stiffness profile and indicated with corresponding reference numbers, including the portions 110-116, 130, 136 (with corresponding portions 110'-116', 130', 136' shown), and a tubular body 140'. Thus, as further discussed herein, the stylet 100' may have the pre-formed first and/or second bends α, β; however, in some embodiments, the stylet 100' may have a pre-formed substantially straight configuration (omitting the first and second bends α, β, in some embodiments, the stylet 100' may have a proximal taper 132' with a first tapered portion 132a' and a second tapered portion 132b' that are connected but have different taper angles. The first tapered portion 132a' may be proximal of the second tapered portion 132b' and transition from the fourth portion 112'. The first tapered portion 132a' may be tapered at a larger angle relative to the longitudinal axis than the second tapered portion 132b'. With the second tapered portion 132b' having a more gradual angle at the proximal end of the narrow segment 130', some of the yielding that occurs in the narrow segment 130' may be transmitted into the larger angle of the first tapered portion 132a'. This reduces the abruptness of the transition. The larger angle of the first taper portion 132a' may also provide a slightly steeper transition to reduce the overall length of the proximal taper 132'. The fifth portion 114' may include the distal segment 136' receiving the conductive coil 160' positioned distal of a first distal taper 134', and a second distal taper 138' between the distal segment 136' and the distal tip 116'. Thus, the distal tip 116' may have substantially the same width or diameter as at least one of the proximal portions 106-112 (as illustrated in the embodiment of FIG. 2). The narrow segment 130' may have a constant width or diameter. The distal segment 136' may have a constant width or diameter greater than the narrow segment 130' and less than the distal tip 116'. For example, the distal segment 136' may have a width or diameter of about 0.009 inch (about 0.22 mm) and the distal tip 116' may be larger and unground, having a width or diameter of about 0.011 inch (about 0.3 mm) increasing the surface area for ECG conductivity.

Figure 17:
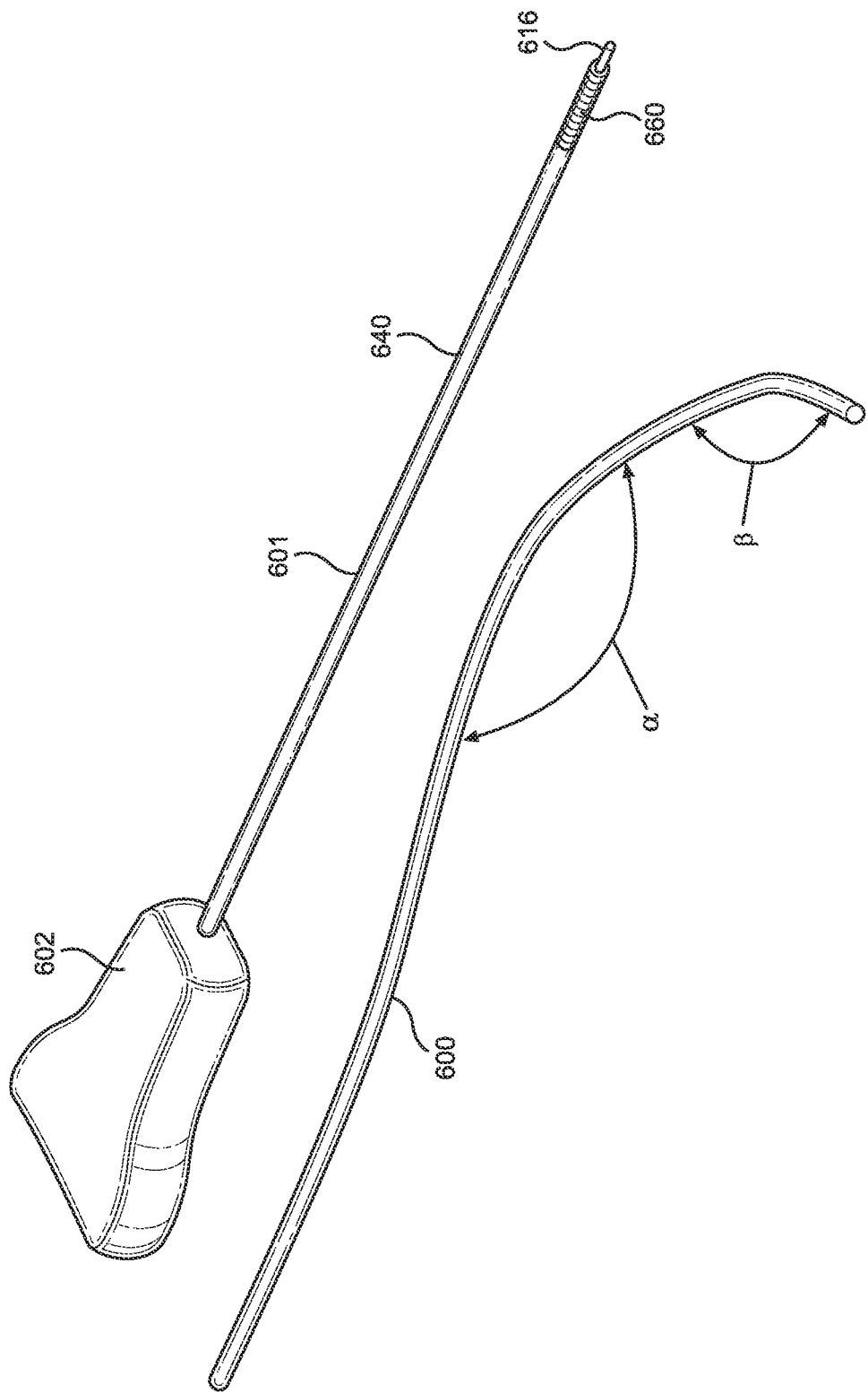
FIG. 17 illustrates an isometric view of an eighth embodiment of a pair of stylets according to the present invention.
Figure 18:
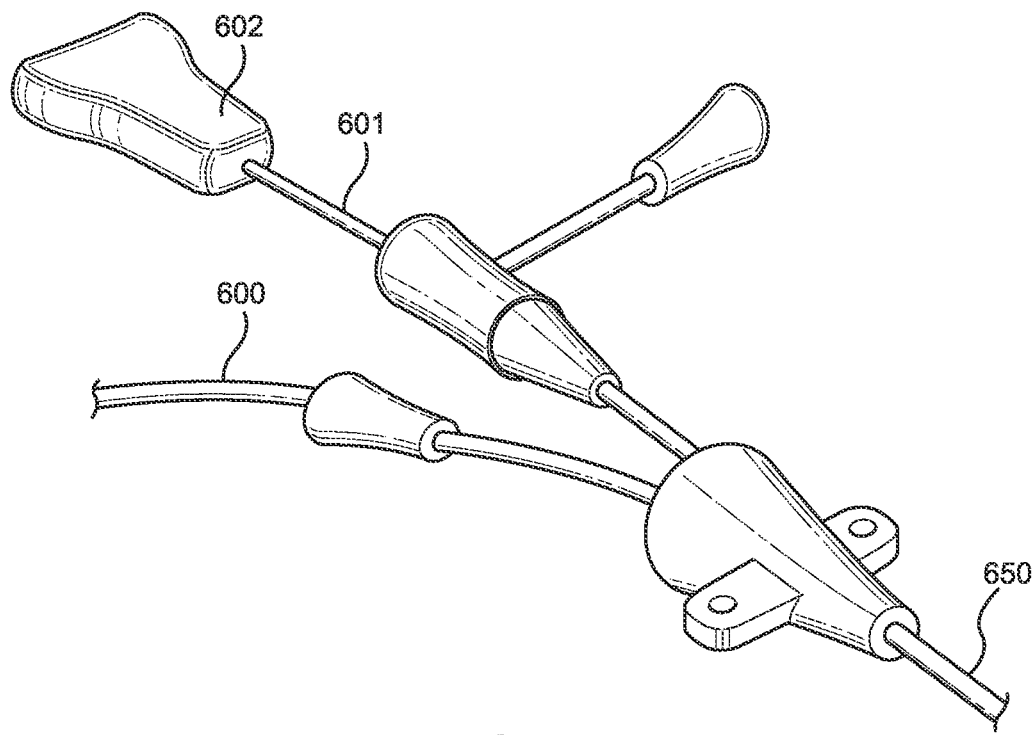
FIG. 18 illustrates a first assembly including the pair of stylets of FIG. 17 in a catheter.
Figure 19:
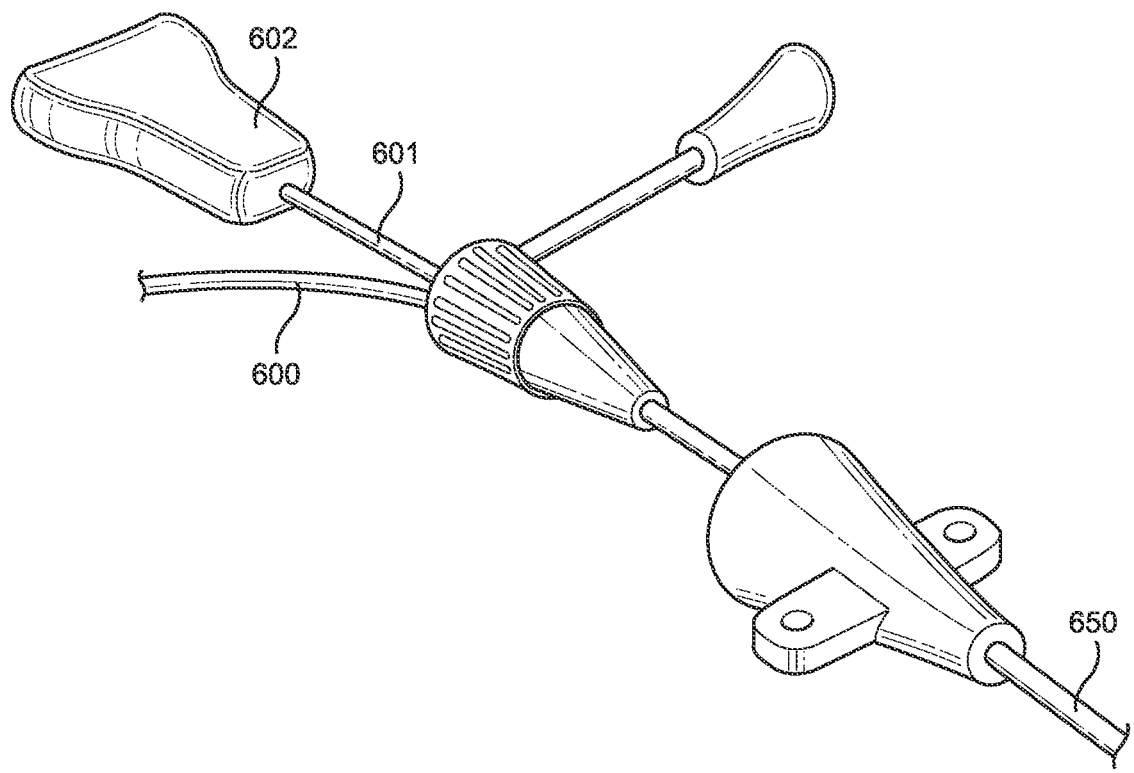
FIG. 19 illustrates a second assembly including the pair of stylets of FIG. 17 in a catheter.

As further illustrated in FIG. 8B, the first taper portion 132a' may have a first length ($L_1$), the second taper portion 132b' may have a second length ($L_2$), the narrow segment 130' may have a third length ($L_3$), the first distal taper 134' may have a fourth length ($L_4$), the distal segment 136' may have a fifth length ($L_5$), the second distal taper 138' may have a sixth length ($L_6$), and the distal tip 116' may have a seventh length ($L_7$). The proximal taper 132' (including the first and second taper portions 132a', 132b') may be more gradual and have a length ($L_1+L_2$) that may be longer than that of the first and/or second distal tapers 134', 138' ($L_4$, $L_6$) and/or combined lengths thereof, allowing the proximal taper 132' to withstand greater forces during insertion and prevent stress concentrations/weak points compromising the strength/performance of the stylet 100'. The lengths of the first and second distal tapers 134', 138' may be reduced to allow the width of the stylet 100' to increase distally over short distances. For example, the proximal taper 132' may be at least about twice the length of at least one of the first and second distal tapers 134', 138' (e.g., both) and less than about six times the length of at least one of the first and second distal tapers 134', 138' (e.g., only the first distal taper 134'). In one illustrative example, the first length ($L_1$) may be about 0.1-0.3 inches, e.g., about 0.2 inches (about 2.5-7.5 mm, e.g., about 5 mm), the second length ($L_2$) may be about 0.1-0.3 inches, e.g., about 0.2 inches (about 2.5-7.5 mm, e.g., about 5 mm), and the third length ($L_3$) may be about 0.1-0.3 inches, e.g., about 0.2 inches (about 2.5-7.5 mm, e.g., about 5 mm). The fourth length ($L_4$) may be about 0.1-0.2 inches, e.g., about 0.14 inches (about 2.5-5 mm, e.g., about 3.5 mm), fifth length ($L_5$) may be about 0.5-0.75 inches, e.g., about 0.635 inches (about 12.5-20 mm, e.g., about 16 mm), the sixth length ($L_6$) may be about 0.005-0.015 inches, e.g., about 0.010 inches (about 0.125-0.4 mm, e.g., about 0.25 mm), and seventh length ($L_7$) may be about 0.05-0.15 inches, e.g., about 0.1 inches (about 1.25-4 mm, e.g., about 2.5 mm). Thus, a length between the proximal end of the narrow segment 130' and the distal end of the stylet 100' may be less than or equal to about 1.6 inches, e.g., about 0.6-1.4 inches (less than or equal to about 4 cm, e.g., about 1.5-3.5 cm) to provide favorable deflection mechanics. The stylet 100' may be made of a nickel titanium alloy (Nitinol™) or stainless steel and have a polytetrafluoroethylene (PTFE) or hydrophobic coating. The stylet 100' may be without a navigation device (omitting the conductive coil 160, leads 162, 164, and tubular body 140), and used as a stiffening wire alongside a separate navigation stylet (e.g., as illustrated in FIGS. 17-19) or by itself (e.g., assembled with the PICC without another stylet).

Figure 9:
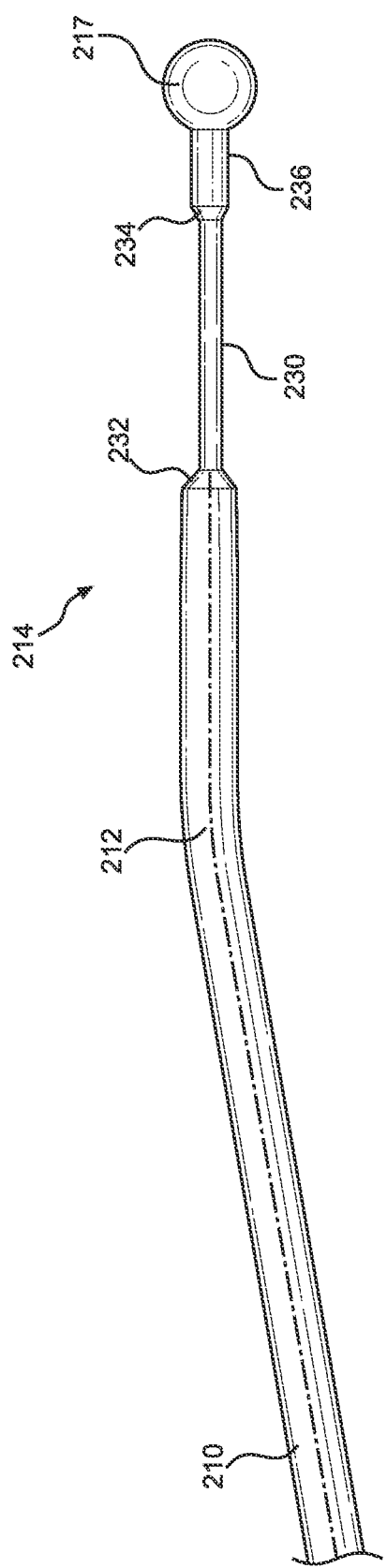
FIG. 9 illustrates a side view of a third embodiment of the stylet according to the present invention.
Figure 10A:
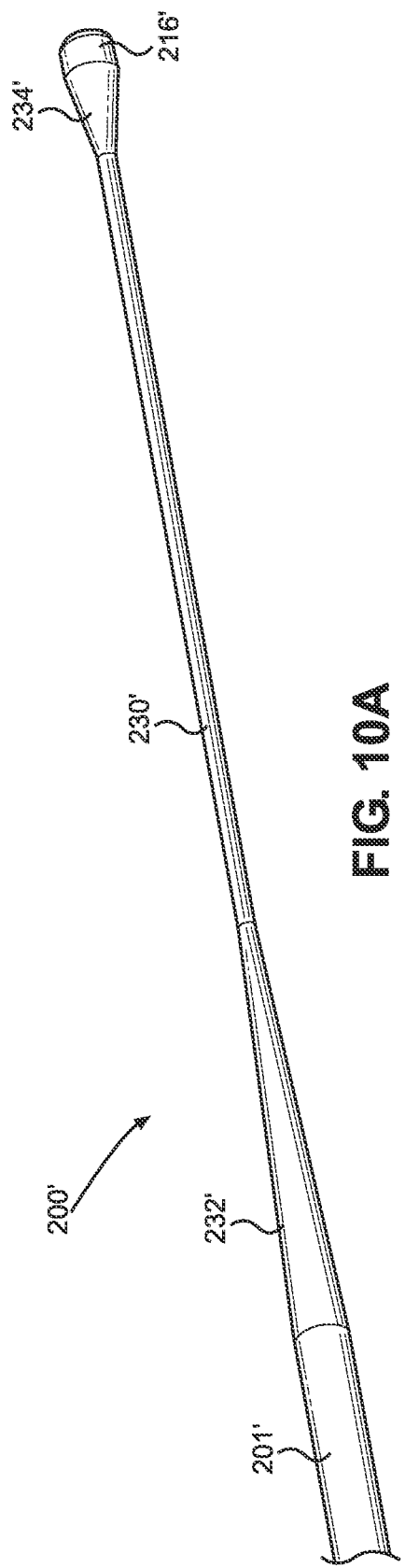
FIGS. 10A-B illustrate views of a fourth embodiment of the stylet according to the present invention.
Figure 10B:
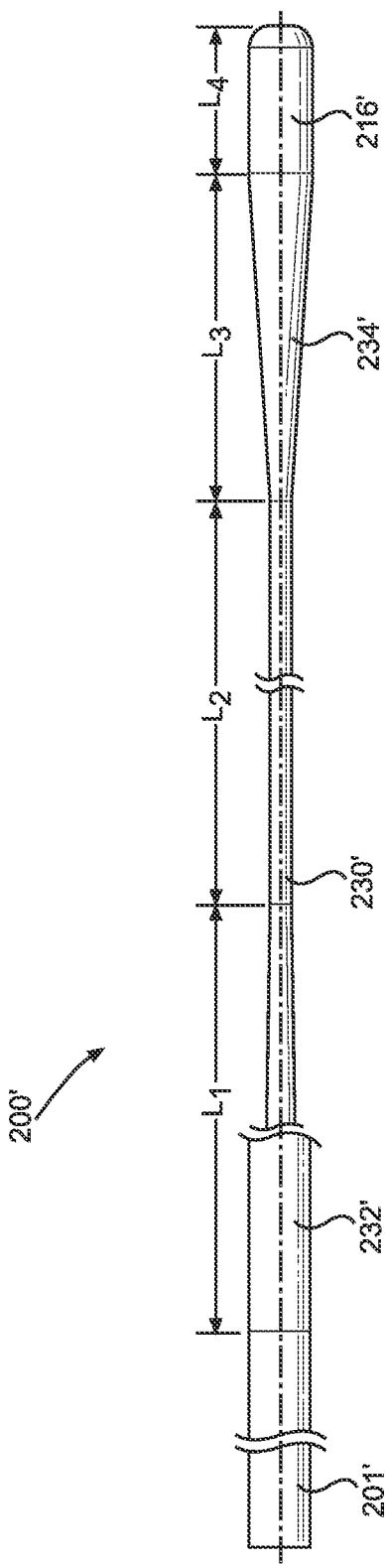

FIG. 9 illustrates a stylet 200 according to a third embodiment of the present invention. The stylet 200 may have similar features as discussed above with regard to at least one of the stylets 100, 100' and incorporated herein (unless otherwise indicated), including the stiffness profile with regard to the stylet 100 and indicated with corresponding reference numbers, including the portions 110-114, 130, 136 (with corresponding portions 210-214, 230, 236 shown), proximal and distal tapers 132, 134 (with corresponding tapers 232, 234 shown). As further discussed herein, the stylet 200 may have the pre-formed first and/or second bends α, β, however, in some embodiments, the stylet 200 may have a preformed substantially straight configuration (omitting the first and second bends α, β). The stylet 200 may have a distal tip 216 including an atraumatic shape, such as a ball weld 217 or a larger diameter with a rounded edge (e.g., as illustrated in FIG. 10A-B). The stylet 200 may be without a navigation device (omitting the conductive coil 160, leads 162, 164, and tubular body 140), and used as a stiffening wire alongside a separate navigation stylet (e.g., as illustrated in FIGS. 17-19) or by itself (e.g., assembled with the PICC without another stylet) 100491 FIGS. 10A-B illustrate a stylet 200' according to a fourth embodiment of the present invention. The stylet 200' may have similar features as discussed above with regard to at least one of the stylets 100, 100', 200 and incorporated herein (unless otherwise indicated). As illustrated, the stylet 200' may include a proximal portion 201' extending from a proximal end (not shown), a proximal taper 232', a narrow segment 230', a distal taper 234', and a distal tip 216' extending to a distal end, in that longitudinal order. As further illustrated, the stylet 200' may have a pre-formed substantially straight configuration (omitting the first and second bends α, β); however, in some embodiments, the stylet 200' may have the pre-formed first and/or second bends α, β, as further discussed herein. The proximal portion 201' may have a first width (or diameter), and the proximal taper 232' may reduce the width of the stylet 200' to a second width (or diameter) less than the first width at the narrow segment 230'. The distal taper 234' may extend from the narrow segment 230' and increase the width of the stylet 200' to a third width (or diameter) at the distal tip 216', where the first and third widths may be substantially the same. The second width of the narrow segment 230' may be less than the first and second widths to provide a floppy portion to allow deflection of the distal portion of the stylet 200', for example, down the RBCV (as further discussed herein). Furthermore, the third width of the distal tip 216' may be large enough to ensure that the distal tip 216' is atraumatic and/or the distal tip 216' may include a substantially cylindrical portion with a rounded and/or tapered circumferential edge.

As further illustrated in FIG. 10B, the proximal taper 232' may have a first length ($L_1$), the narrow segment 230' may have a second length ($L_2$), the distal taper 234' may have a third length ($L_3$), and the distal tip 216' may have a fourth length ($L_4$). The proximal taper 232' may be more gradual and the first length ($L_1$) may be longer than the third length ($L_3$), allowing the proximal taper 232' to withstand greater forces during insertion and prevent stress concentrations/weak points compromising the strength/performance of the stylet 200'. The third length ($L_3$) of the distal taper 234' may be reduced to allow the width of the stylet 200' to increase from the narrow segment 230' to the distal tip 216' over a short distance. For example, the proximal taper 232' may be at least about twice the length of the distal taper 234' and less than about six times the length of the distal taper 234'. In one illustrative example, the first length ($L_1$) may be about 0.2-0.6 inches, e.g., about 0.4 inches (about 5-15 mm, e.g., about 10 mm), the second length ($L_2$) may be about 0.6-1.0 inches, e.g., about 0.8 inch (about 15-25 mm, e.g., about 20 mm), the third length ($L_3$) may be about 0.04-0.2 inches, e.g., about 0.08 inches (about 1 to 5 mm, e.g., about 2 mm), and the fourth length ($L_4$) may be about 0.02-0.06 inches, about 0.04 inches (about 0.5-1.5 mm, e.g., about 1 mm), Thus, a fifth length ($L_2+L_3+L_4$) between the proximal end of the narrow segment 230' and the distal tip of the stylet 200' may be less than or equal to about 1.6 inches, e.g. about 0.6-1.4 inches (less than or equal to about 40 mm, e.g., about 15-35 mm) to provide favorable deflection mechanics. The stylet 200' may be made of a nickel titanium alloy or stainless steel and have a polytetrafluoroethylene (PTFE) or hydrophobic coating. The stylet 200' may be without a navigation device (omitting the conductive coil 160, leads 162, 164, and tubular body 140), and used as a stiffening wire alongside a separate navigation stylet (e.g., as illustrated in FIGS. 17-19) or by itself (e.g., assembled with the PICC without another stylet).

Figure 12:
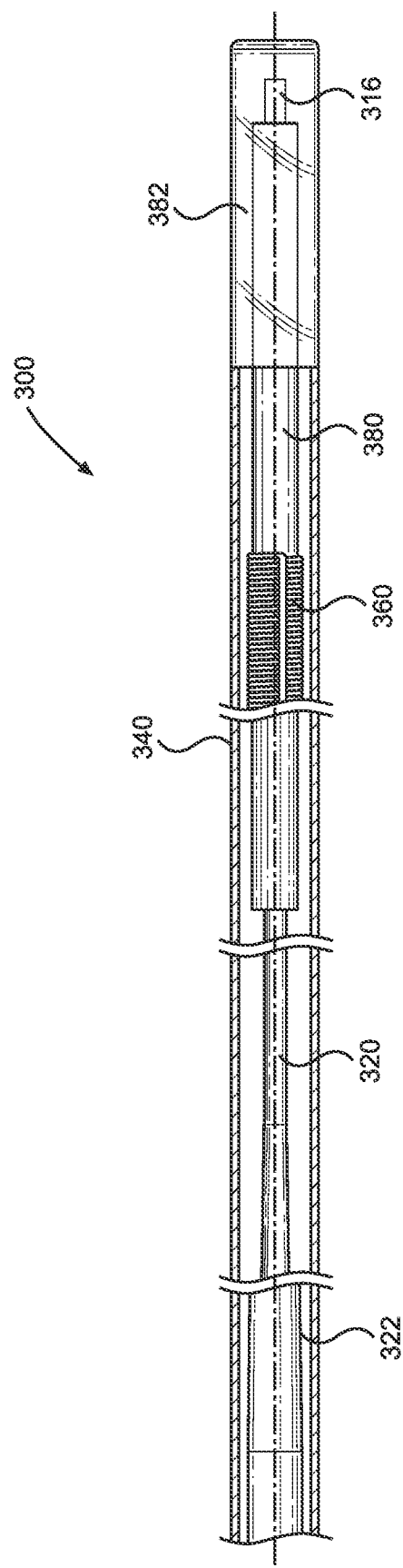
FIG. 12 illustrates a side view of the stylet of FIGS. 11A-B.

FIGS. 11A-12 illustrate a stylet 300 according to a fifth embodiment of the present invention. The stylet 300 may include a core wire 320, a tubular body 340, a conductive coil 360, and a magnetic hypotube 380. As illustrated, the core wire 320 may be received inside of the magnetic hypotube 380, and the core wire 320 and magnetic hypotube 380 may be received in the tubular body 340. The stylet 300 may have similar features as discussed above with regard to at least one of the stylets 100, 100', 200 and incorporated herein (unless otherwise indicated), including the body and tip curve profile, sizes, and stiffness profile with regard to the stylet 100, the portions 110-116, 130, and the first and second bends a, The core wire 320 may be made of a nickel titanium alloy, providing the additional advantage of being a kink-resistant alloy, but is inherently non-magnetic. Therefore, in order to provide the desired properties of the present application (e.g., navigation/electronic stylet with curve profile and appropriate grind profile), the magnetic hypotube 380 may be provided over a distal portion of the core wire 320. The magnetic hypotube 380 may be short and made out of a magnetic permeable material, such as stainless steel or other similar materials. The core wire 320 may include a taper 322 disposed proximally of the magnetic hypotube 380, and the hypotube 380 may be disposed proximally of a distal tip 326 of the core wire 320. The conductive coil 360 may be wound over the hypotube 380 to provide passive sensor coil capabilities for navigation, as discussed herein.

The core wire 320 and the magnetic hypotube 380 may extend distally out of the tubular body 340 and be at least partially covered with a conductive epoxy 382 at a portion of the stylet 300 distal of the tubular body 340. In some embodiments, the conductive epoxy 382 may secure the core wire 320, tubular body 340, and magnetic hypotube 380 together and be configured to conduct the ECG signals to the tip portion 316. However, in some embodiments, a second epoxy (not shown) may join the core wire 320 and the magnetic hypotube 380, while the conductive epoxy 382 covers the tip portion 316 to conduct the ECG signals. Additionally or alternatively, the core wire 320 and hypotube 380 may be welded together with enough exposed metal at the tip portion 316 to conduct the ECG signals. Additionally or alternatively, a conductive hypotube (not shown) may be provided to conduct the ECG signals.

Figure 14A:
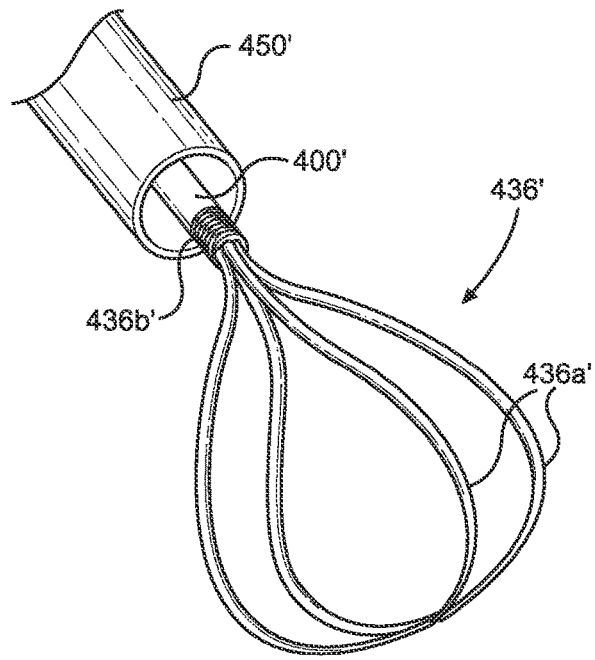
FIGS. 14A-C illustrate a first variation of the stylet of FIGS. 13A-B.
Figure 14B:
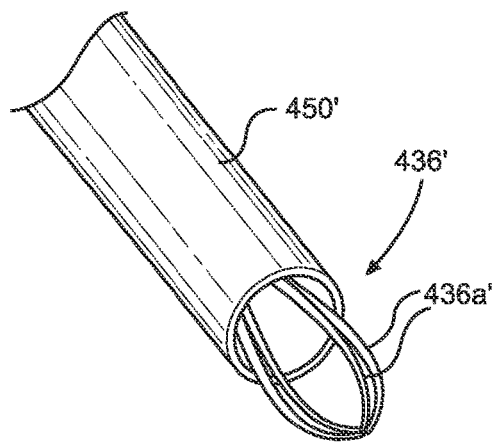
Figure 14C:
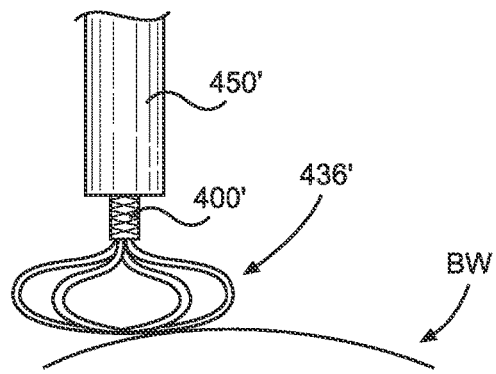
Figure 15:
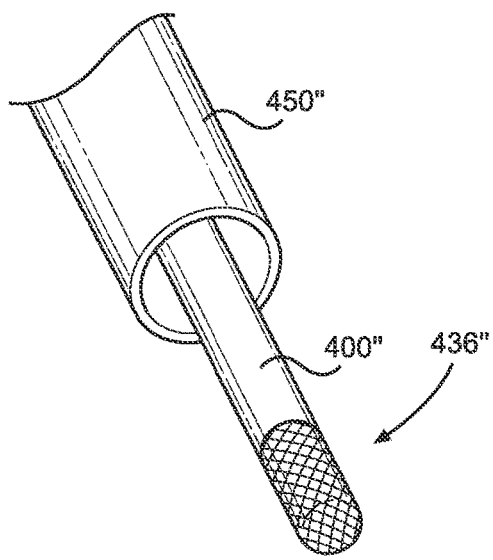
FIG. 15 illustrates a second variation of the stylet of FIGS. 13A-B.

FIGS. 13A-B illustrate a stylet 400 and a catheter 450 according to a sixth embodiment of the present invention, The stylet 400 may have similar features as discussed above with regard to at least one of the stylets 100, 100', 200, 300 and incorporated herein (unless otherwise indicated), including a core wire, a tubular body 440, and the first and second bends α, β. The stylet 400 may further include an atraumatic distal segment 436 that reduces trauma to a back wall (BW) at the confluence (C) and facilitates deflection of the distal segment 436 down/off the back wall (BW) toward the RBVC, compared to a stylet/PICC assembly with a leading tip comprised externally of a PICC only (e.g., without an atraumatic distal segment). The distal segment 436 may be soft and/or substantially compressible along the longitudinal axis of the stylet 400 and extend distally of the distal end of the catheter 450 to contact the vein first. For example, as illustrated in FIGS. 13A-B, the distal segment 436 may have a J-shape that is configured to resiliently deflect when contacting the back wall (BW) and reduce "tenting" compared to a more pointed distal portion. The core wire may extend through the distal segment 436, such that a distal end 416 of the Core wire extends out of the tubular body 440 in a proximal direction. The distal end 416 may be exposed to allow for conduction of ECG signals, as further discussed herein. In another embodiment, as illustrated in FIGS. 14A-C, a stylet 400' received in a catheter 450' may include a distal segment 436' including a plurality of flexible members 436a' (e.g., wires) having a curved or looped configuration forming a basket. The flexible members 436a' may extend distal from a tubular portion 436b' and be joined at a distal tip of the stylet 400' and/or be looped back proximally to the tubular portion 436b'. The flexible members 436a' may be resiliently expandable (as illustrated in FIG. 14A) and be collapsed when pulled back into the catheter 450' (as illustrated in FIG. 14B). The flexible members 436a' may be conductive of ECG signals for navigation purposes, as discussed herein. Similar to the embodiment of FIG. 13A-B, the distal segment 436' may resiliently deflect when contacting the back wall (BW) (as illustrated in FIG. 14C) at the confluence (C) and reduce "tenting". In yet another embodiment, a stylet 400" received in a catheter 450" may include a distal segment 436" of a soft mesh of a plurality of members. The distal segment 436" may resiliently deflect when contacting the back wall (BW) at the confluence (C) and reduce "tenting". The distal segment 436" may further be conductive of ECG signals, as discussed herein. The function of the distal segment 436, 436', 436" may supplement or replace the functionality of the first bend α and/or second bend β, thus in some embodiments, the first bend α and/or second bend β may be omitted, such that the stylet 400 may have a pre-formed straight configuration.

Figure 16:
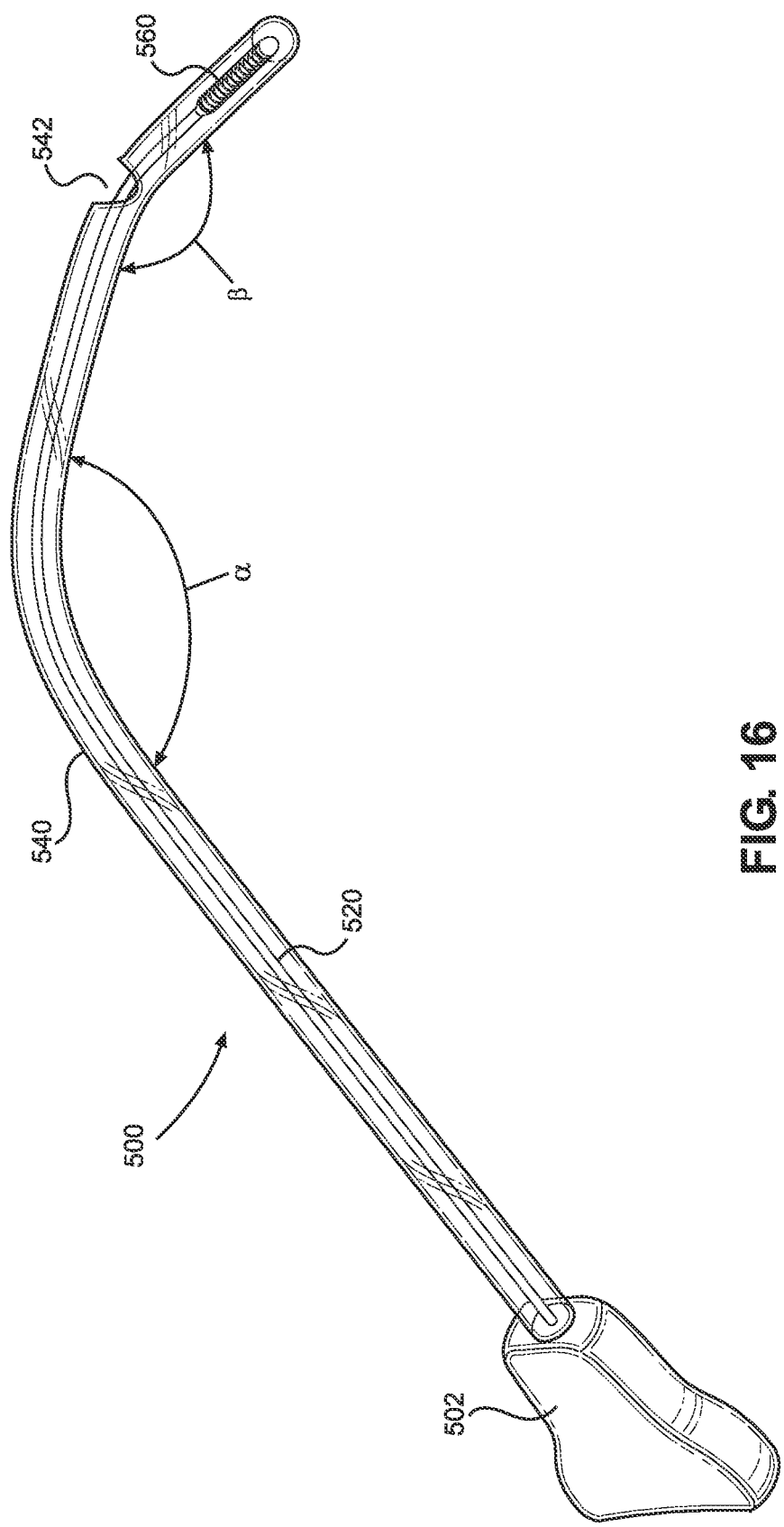
FIG. 16 illustrates an isometric view of a seventh embodiment of a stylet in a catheter according to the present invention.

FIG. 16 illustrates a stylet 500 according to a seventh embodiment of the present invention. The stylet 500 may have similar features as discussed above with regard to at least one of the stylets 100, 100', 200, 300, 400 and incorporated herein (unless otherwise indicated), including a core wire 520, a tubular body 540, a housing member 502, and first and second bends α, β. As illustrated, the distal end of the core wire 520 may be enclosed by the tubular body 540 reducing trauma and providing a lubricous contact with the back wall (BW) at the confluence (C). To provide the ECG signal conduction, the tubular body 540 may include an opening 542 through a side wall of the tubular body 540 between the proximal and distal ends of the tubular body 540. The opening 542 may allow for ECG signals from the body to contact the core wire 520. For example, the opening 542 may be distal of the first and/or second bends α, β (e.g., at the second bend β, as illustrated) in order to detect the location of the distal tip of the stylet 500. Thus, the core wire 520 may be configured to conduct the ECG signal for navigation, while avoiding any trauma caused by an exposed distal tip of the core wire 520, if it were sharp.

FIGS. 17-19 illustrate a pair of stylets 600, 601 according to an eighth embodiment of the present invention. The first stylet 600 may be configured to be conductive of an ECG signal for navigation, and the second stylet 601 may be configured to shape a catheter 650 to facilitate threading into the SVC, as further discussed herein with regard to at least one of the stylets 100, 100', 200, 300, 400, 500 and incorporated herein (unless otherwise indicated). The first stylet 600 may include a housing 602, a tubular body 640, a core wire disposed within the tubular body 640 and having a distal tip 616 to conduct the ECG signal, and conductive coil 660 around the core wire in the tubular body 640, as further discussed herein with regard to at least one of the stylets 100, 100', 200, 300, 400, 500. The second stylet 601 may be a non-conductive elongated member or wire pre-formed with the first and second bends α, β to facilitate threading the catheter 650 past the confluence (C). As illustrated in the first assembly of FIG. 18, the first and second stylets 600, 601 may be inserted in separate lumens of the catheter 650. As further illustrated in the second assembly of FIG. 19, the first and second stylets 600, 601 may be inserted into the same lumen of the catheter 650. In either assembly, separating the functions (e.g., ECG navigation and threadability of the catheter) into the first and second stylets 600, 601 may facilitate manufacturing, for example, by allowing different materials with optimized mechanical and/or electrical properties to perform each function.

The many features and advantages of the invention are apparent from the detailed specification, and thus, it is intended by the appended claims to cover all such features and. advantages of the invention which fall within the true spirit and scope of the invention. Further, since numerous modifications and variations will readily occur to those skilled in the art, it is not desired to limit, the invention to the exact construction and operation illustrated and described, and accordingly, all suitable modifications and equivalents may be resorted to, falling within the scope of the invention.

What is claimed is:

1. An assembly for accessing a superior vena cava of a patient without visualization of a vasculature of the patient, the assembly comprising:

a stylet including a housing member and an elongated body configured to be inserted through the vasculature of the patient, the elongated body extending from the housing member to a distal tip and including a core wire disposed within a tubular body, the core wire having a pre-formed shape in a first state and a straightened shape in a second state, wherein a potential energy of the core wire in the first state is less than the potential energy of the core wire in the second state, the core wire comprising:

a first portion extending distally from the housing member and having a substantially straight shape in the first state;

a second portion extending distally from the first portion and having a first pre-formed bend in the first state;

a third portion extending distally from the second portion and having a substantially straight shape in the first state;

a fourth portion extending distally from the third portion and having a second pre-formed bend in the first state;

a fifth portion extending distally from the fourth portion to the distal tip, the fifth portion having a substantially straight shape in the first state and including a narrow segment with a reduced width or diameter relative to the first through fourth portions, and a distal segment between the narrow segment and the distal tip, the distal segment having a width or diameter greater than the respective width or diameter of the narrow segment, the narrow segment being configured to increase deflection of the distal tip, and the distal tip having a width or diameter greater than the respective width or diameter of the distal segment; and a first distal taper with an increasing width or diameter in a distal direction, the first distal taper disposed between the narrow segment and the distal segment, and a second distal taper with an increasing width or diameter in the distal direction, the second distal taper disposed between the distal segment and the distal tip;

wherein the first pre-formed bend and the second pre-formed bend are in the same plane and the same rotational direction, wherein the first pre-formed bend defines a first angle in the range of 55-70° between a longitudinal axis of the first portion and a longitudinal axis of the third portion, wherein the second pre-formed bend defines a second angle in the rage of 8- 15° between the longitudinal axis of the third portion and a longitudinal axis of the fifth portion, and wherein an arc length of the first pre-formed bend is in the range of 3-7 inches.

2. The assembly according to claim 1, wherein an arc length of the second pre-formed bend is in the range of 0.2-0.5 inches.

3. The assembly according to claim 1, wherein the first and second pre-formed bends are configured to automatically align the distal tip at an approach angle directed toward a lower portion of a back wall of the vasculature to assist the distal tip in pointing down towards the superior vena cava during insertion of the stylet into the vasculature.

4. The assembly according to claim 1, wherein the core wire has minimal or no-torqueability.

5. The assembly according to claim 1, wherein the narrow segment is straight and has a constant width or diameter.

6. The assembly according to claim 5, wherein the narrow segment of the fifth portion includes a proximal end having a proximal taper with a decreasing width or diameter.

7. The assembly according to claim 6, wherein the narrow segment of the fifth portion includes a distal end having the first distal taper with an increasing width or diameter.

8. The assembly according to claim 5, wherein the narrow segment has a rounded and/or flattened cross-section.

9. The assembly according to claim 1, further comprising a conductive coil disposed over and around the distal segment of the core wire to provide passive sensor coil capabilities for navigation.

10. The assembly according to claim 9, wherein the tubular body encloses the conductive coil.

11. The assembly according to claim 10, wherein a distal end of the tubular body is bonded to the core wire distal of the conductive coil.

12. The assembly according to claim 1, wherein the distal tip has a width or diameter greater than the respective width or diameter of the distal segment.

13. The assembly according to claim 1, wherein the core wire is conductive of an electrocardiogram (ECG) signal, and the distal tip of the core wire extends distally of the tubular body or the tubular body has an opening in a sidewall to allow fluid contact with the core wire.

14. The assembly according to claim 1, further comprising a conductive coil disposed over and around the core wire to provide passive sensor coil capabilities for navigation.

15. The assembly according to claim 14, wherein the tubular body encloses the conductive coil.

16. The assembly according to claim 15, wherein a distal end of the tubular body is bonded to the core wire distal of the conductive coil.

17. The assembly according to claim 14, wherein the core wire is conductive of an electrocardiogram (ECG) signal, and the distal tip of the core wire extends distally of the tubular body or the tubular body has an opening in a sidewall to allow fluid contact with the core wire.

18. The assembly according to claim 1, wherein the core wire comprises a nickel titanium alloy.

19. The assembly according to claim 1, wherein the first angle of the first pre-formed bend is about 60° between the longitudinal axis of the first portion and the longitudinal axis of the third portion.

20. The assembly according to claim 1, wherein the second angle of the second pre-formed bend is about 10° between the longitudinal axis of the third portion and the longitudinal axis of the fifth portion.

21. The assembly according to claim 1, wherein a portion of the core wire is bonded to a portion of the tubular body.

* * * * *